United States Patent
Hossainy et al.

(10) Patent No.: US 9,242,005 B1
(45) Date of Patent: *Jan. 26, 2016

(54) PRO-HEALING AGENT FORMULATION COMPOSITIONS, METHODS AND TREATMENTS

(75) Inventors: Syed Hossainy, Fremont, CA (US); Florian Niklas Ludwig, Mountain View, CA (US); Stephen Pacetti, San Jose, CA (US); Paul Consigny, San Jose, CA (US); Fozan El-Nounou, Santa Clara, CA (US); Thierry Glauser, Redwood City, CA (US); Jessica DesNoyer, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 696 days.

This patent is subject to a terminal disclaimer.

(21) Appl. No.: 11/507,860

(22) Filed: Aug. 21, 2006

(51) Int. Cl.
*A61M 31/00* (2006.01)
*A61K 47/42* (2006.01)
*A61K 47/48* (2006.01)
*A61M 5/178* (2006.01)

(52) U.S. Cl.
CPC ............. *A61K 47/42* (2013.01); *A61K 47/48* (2013.01); *A61M 5/178* (2013.01); *A61M 31/00* (2013.01)

(58) Field of Classification Search
CPC ....... A61K 47/42; A61K 47/48; A61K 47/52; A61K 31/752; A61K 31/734; A61M 31/00; A61M 5/178; A61P 2/00; A61P 9/22
See application file for complete search history.

(56) References Cited

U.S. PATENT DOCUMENTS

| | | | |
|---|---|---|---|
| 2,512,569 | A | 6/1950 | Saffir |
| 3,144,868 | A | 8/1964 | Jascalevich |
| 3,584,624 | A | 6/1971 | de Ciutiis |
| 3,780,733 | A | 12/1973 | Martinez-Manzor |
| 3,804,097 | A | 4/1974 | Rudie |
| 3,890,976 | A | 6/1975 | Bazell et al. |

(Continued)

FOREIGN PATENT DOCUMENTS

| | | |
|---|---|---|
| EP | 0331584 | 9/1989 |
| EP | 0835667 | 4/1998 |

(Continued)

OTHER PUBLICATIONS

Csonka et al., (Acta Morphologica Hungarica. 1987;32(1-2):31-35).*

(Continued)

*Primary Examiner* — Cherie M Stanfield
(74) *Attorney, Agent, or Firm* — Randy Shen, Esq.; Blakely Sokoloff Taylor & Zafman LLP

(57) ABSTRACT

Pro-healing agent formulation compositions, methods and treatments for enhancing vascular healing are disclosed herein. In some embodiments, a pro-healing agent is encapsulated, suspended, disposed within or loaded into a biodegradable carrier for sustained-release delivery to a denuded or damaged endothelium treatment area in a blood vessel. In some applications, the pro-healing agent can accelerate re-endothelialization of a denuded vascular region. In some applications, the pro-healing agent can assist in the regaining of endothelium functionality. The formulation can be delivered by a delivery assembly such as an infusion catheter, a porous balloon catheter, a needle injection catheter, a double balloon catheter or the like.

21 Claims, 9 Drawing Sheets

(56) References Cited

U.S. PATENT DOCUMENTS

| | | |
|---|---|---|
| 4,141,973 A | 2/1979 | Balazs |
| 4,617,186 A | 10/1986 | Schafer et al. |
| 4,794,931 A | 1/1989 | Yock |
| 4,818,291 A | 4/1989 | Iwatsuki et al. |
| 4,842,590 A | 6/1989 | Tanabe et al. |
| 5,000,185 A | 3/1991 | Yock |
| 5,024,234 A | 6/1991 | Leary et al. |
| 5,026,350 A | 6/1991 | Tanaka et al. |
| 5,049,130 A | 9/1991 | Powell |
| 5,092,848 A | 3/1992 | DeCiutiis |
| 5,100,185 A | 3/1992 | Menke et al. |
| 5,109,859 A | 5/1992 | Jenkins |
| 5,116,317 A | 5/1992 | Carson et al. |
| 5,128,326 A | 7/1992 | Balazs et al. |
| 5,171,217 A | 12/1992 | March et al. |
| 5,202,745 A | 4/1993 | Sorin et al. |
| 5,203,338 A | 4/1993 | Jang |
| 5,242,427 A | 9/1993 | Bilweis |
| 5,270,300 A | 12/1993 | Hunziker |
| 5,291,267 A | 3/1994 | Sorin et al. |
| 5,306,250 A | 4/1994 | March et al. |
| 5,321,501 A | 6/1994 | Swanson et al. |
| 5,328,955 A | 7/1994 | Rhee et al. |
| 5,336,252 A | 8/1994 | Cohen |
| 5,354,279 A | 10/1994 | Hofling |
| 5,365,325 A | 11/1994 | Kumasaka et al. |
| 5,372,138 A | 12/1994 | Crowley et al. |
| 5,380,292 A | 1/1995 | Wilson |
| 5,419,777 A | 5/1995 | Hofling et al. |
| 5,437,632 A | 8/1995 | Engelson |
| 5,455,039 A | 10/1995 | Edelman et al. |
| 5,459,570 A | 10/1995 | Swanson et al. |
| 5,464,395 A | 11/1995 | Faxon et al. |
| 5,465,147 A | 11/1995 | Swanson |
| 5,485,486 A | 1/1996 | Gilhousen et al. |
| 5,499,630 A | 3/1996 | Hiki et al. |
| 5,516,532 A | 5/1996 | Atala et al. |
| 5,540,912 A | 7/1996 | Roorda et al. |
| 5,546,948 A | 8/1996 | Hamm et al. |
| 5,554,389 A | 9/1996 | Badylak et al. |
| 5,575,815 A | 11/1996 | Slepian et al. |
| 5,580,714 A | 12/1996 | Polovina |
| 5,580,856 A | 12/1996 | Prestrelski et al. |
| 5,588,432 A | 12/1996 | Crowley |
| 5,621,610 A | 4/1997 | Moore et al. |
| 5,631,011 A | 5/1997 | Wadstrom |
| 5,642,234 A | 6/1997 | Altman et al. |
| 5,655,548 A | 8/1997 | Nelson et al. |
| 5,667,778 A | 9/1997 | Atala |
| 5,669,883 A | 9/1997 | Scarfone et al. |
| 5,672,153 A | 9/1997 | Lax et al. |
| 5,676,151 A | 10/1997 | Yock |
| 5,693,029 A | 12/1997 | Leonhardt |
| 5,722,403 A | 3/1998 | McGee et al. |
| 5,725,551 A | 3/1998 | Myers et al. |
| 5,730,732 A | 3/1998 | Sardelis et al. |
| 5,740,808 A | 4/1998 | Panescu et al. |
| 5,749,915 A | 5/1998 | Slepian |
| 5,772,665 A | 6/1998 | Glad et al. |
| 5,785,689 A | 7/1998 | De Toledo et al. |
| 5,795,331 A | 8/1998 | Cragg et al. |
| 5,810,885 A | 9/1998 | Zinger |
| 5,811,533 A | 9/1998 | Gold et al. |
| 5,827,313 A | 10/1998 | Ream et al. |
| 5,843,156 A | 12/1998 | Slepian et al. |
| 5,874,500 A | 2/1999 | Rhee et al. |
| 5,879,713 A | 3/1999 | Roth et al. |
| 5,900,433 A | 5/1999 | Igo et al. |
| 5,906,934 A | 5/1999 | Grande et al. |
| 5,919,449 A | 7/1999 | Dinsmore |
| 5,935,160 A | 8/1999 | Auricchio et al. |
| 5,939,323 A | 8/1999 | Valentini et al. |
| 5,941,868 A | 8/1999 | Kaplan et al. |
| 5,957,941 A | 9/1999 | Ream |
| 5,968,064 A | 10/1999 | Selmon |
| 5,979,449 A | 11/1999 | Steer |
| 5,980,887 A * | 11/1999 | Isner et al. .................. 424/93.7 |
| 5,981,568 A | 11/1999 | Kunz et al. |
| 5,984,908 A | 11/1999 | Davis et al. |
| 5,997,536 A | 12/1999 | Osswald et al. |
| 6,022,540 A | 2/2000 | Bruder et al. |
| 6,045,565 A | 4/2000 | Ellis et al. |
| 6,050,949 A | 4/2000 | White et al. |
| 6,051,071 A | 4/2000 | Charvet et al. |
| 6,051,648 A | 4/2000 | Rhee et al. |
| 6,056,744 A | 5/2000 | Edwards |
| 6,058,329 A | 5/2000 | Salo et al. |
| 6,060,053 A | 5/2000 | Atala |
| 6,071,305 A | 6/2000 | Brown et al. |
| 6,086,582 A | 7/2000 | Altman et al. |
| 6,093,177 A | 7/2000 | Javier, Jr. et al. |
| 6,099,563 A | 8/2000 | Zhong |
| 6,099,864 A | 8/2000 | Morrison et al. |
| 6,102,887 A | 8/2000 | Altman |
| 6,102,904 A | 8/2000 | Vigil et al. |
| 6,102,926 A | 8/2000 | Tartaglia et al. |
| 6,120,520 A | 9/2000 | Saadat et al. |
| 6,120,904 A | 9/2000 | Hostettler et al. |
| 6,127,448 A | 10/2000 | Domb |
| 6,133,231 A | 10/2000 | Ferrara et al. |
| 6,134,003 A | 10/2000 | Tearney et al. |
| 6,146,373 A | 11/2000 | Cragg et al. |
| 6,151,525 A | 11/2000 | Soykan |
| 6,152,141 A | 11/2000 | Stevens et al. |
| 6,153,428 A | 11/2000 | Gustafsson et al. |
| 6,159,443 A | 12/2000 | Hallahan et al. |
| 6,162,202 A | 12/2000 | Sicurelli et al. |
| 6,175,669 B1 | 1/2001 | Colston et al. |
| 6,177,407 B1 | 1/2001 | Rodgers et al. |
| 6,179,809 B1 | 1/2001 | Khairkhahan et al. |
| 6,183,432 B1 | 2/2001 | Milo |
| 6,183,444 B1 | 2/2001 | Glines et al. |
| 6,187,330 B1 | 2/2001 | Wang et al. |
| 6,190,353 B1 | 2/2001 | Makower et al. |
| 6,191,144 B1 | 2/2001 | Isner |
| 6,192,271 B1 | 2/2001 | Hayman |
| 6,193,763 B1 | 2/2001 | Mackin |
| 6,197,324 B1 | 3/2001 | Crittenden |
| 6,201,608 B1 | 3/2001 | Mandella et al. |
| 6,206,893 B1 | 3/2001 | Klein et al. |
| 6,206,914 B1 | 3/2001 | Soykan et al. |
| 6,207,180 B1 | 3/2001 | Ottoboni et al. |
| 6,210,392 B1 | 4/2001 | Vigil et al. |
| 6,217,527 B1 | 4/2001 | Selmon et al. |
| 6,217,554 B1 | 4/2001 | Green |
| 6,221,049 B1 | 4/2001 | Selmon et al. |
| 6,231,546 B1 | 5/2001 | Milo et al. |
| 6,235,000 B1 | 5/2001 | Milo et al. |
| 6,241,710 B1 | 6/2001 | Van Tassel et al. |
| 6,251,104 B1 | 6/2001 | Kesten et al. |
| 6,283,947 B1 | 9/2001 | Mirzaee |
| 6,287,285 B1 | 9/2001 | Michal et al. |
| 6,290,729 B1 | 9/2001 | Slepian et al. |
| 6,296,602 B1 | 10/2001 | Headley |
| 6,299,604 B1 | 10/2001 | Ragheb et al. |
| 6,309,370 B1 | 10/2001 | Haim et al. |
| 6,312,725 B1 | 11/2001 | Wallace et al. |
| 6,315,994 B2 | 11/2001 | Usala et al. |
| 6,323,278 B2 | 11/2001 | Rhee et al. |
| RE37,463 E | 12/2001 | Altman |
| 6,328,229 B1 | 12/2001 | Duronio et al. |
| 6,331,309 B1 | 12/2001 | Jennings, Jr. et al. |
| 6,333,194 B1 | 12/2001 | Levy et al. |
| 6,334,872 B1 | 1/2002 | Termin et al. |
| 6,338,717 B1 | 1/2002 | Ouchi |
| 6,346,098 B1 | 2/2002 | Yock et al. |
| 6,346,099 B1 | 2/2002 | Altman |
| 6,346,515 B1 | 2/2002 | Pitaru et al. |
| 6,358,247 B1 | 3/2002 | Altman et al. |
| 6,358,258 B1 | 3/2002 | Arcia et al. |
| 6,360,129 B1 | 3/2002 | Ley et al. |
| 6,368,285 B1 | 4/2002 | Osadchy et al. |
| 6,371,935 B1 | 4/2002 | Macoviak et al. |
| 6,371,992 B1 | 4/2002 | Tanagho et al. |

(56) References Cited

U.S. PATENT DOCUMENTS

| | | | |
|---|---|---|---|
| 6,379,379 B1 | 4/2002 | Wang | |
| 6,385,476 B1 | 5/2002 | Osadchy et al. | |
| 6,391,052 B2 | 5/2002 | Buirge et al. | |
| 6,395,023 B1 | 5/2002 | Summers | |
| 6,409,716 B1 | 6/2002 | Sahatjian et al. | |
| 6,416,510 B1 | 7/2002 | Altman et al. | |
| 6,425,887 B1 | 7/2002 | McGuckin et al. | |
| 6,432,119 B1 | 8/2002 | Saadat | |
| 6,436,135 B1 | 8/2002 | Goldfarb | |
| 6,440,947 B1 | 8/2002 | Barron et al. | |
| 6,443,941 B1 | 9/2002 | Slepian et al. | |
| 6,443,949 B2 | 9/2002 | Altman | |
| 6,447,504 B1 | 9/2002 | Ben-Haim et al. | |
| 6,458,095 B1 | 10/2002 | Wirt et al. | |
| 6,458,098 B1 | 10/2002 | Kanesaka | |
| 6,464,862 B2 | 10/2002 | Bennett et al. | |
| 6,465,001 B1 | 10/2002 | Hubbell et al. | |
| 6,478,775 B1 | 11/2002 | Galt et al. | |
| 6,478,776 B1 | 11/2002 | Rosenman et al. | |
| 6,482,231 B1 | 11/2002 | Abatangelo et al. | |
| 6,485,481 B1 | 11/2002 | Pfeiffer | |
| 6,494,862 B1 | 12/2002 | Ray et al. | |
| 6,514,217 B1 | 2/2003 | Selmon et al. | |
| 6,544,227 B2 | 4/2003 | Sahatjian et al. | |
| 6,544,230 B1 | 4/2003 | Flaherty et al. | |
| 6,548,081 B2 | 4/2003 | Sadozai et al. | |
| 6,554,801 B1 | 4/2003 | Steward et al. | |
| 6,569,441 B2 * | 5/2003 | Kunz et al. | 424/423 |
| 6,599,267 B1 | 7/2003 | Ray et al. | |
| 6,602,241 B2 | 8/2003 | Makower et al. | |
| 6,616,869 B2 | 9/2003 | Mathiowitz et al. | |
| 6,620,927 B2 | 9/2003 | Bulpitt et al. | |
| 6,624,245 B2 | 9/2003 | Wallace et al. | |
| 6,628,988 B2 | 9/2003 | Kramer et al. | |
| 6,629,947 B1 | 10/2003 | Sahatjian et al. | |
| 6,632,457 B1 | 10/2003 | Sawhney | |
| 6,635,267 B1 | 10/2003 | Miyoshi et al. | |
| 6,660,034 B1 | 12/2003 | Mandrusov et al. | |
| 6,663,881 B2 | 12/2003 | Kunz et al. | |
| 6,682,730 B2 | 1/2004 | Mickel et al. | |
| 6,689,608 B1 | 2/2004 | Mikos et al. | |
| 6,692,466 B1 | 2/2004 | Chow et al. | |
| 6,702,744 B2 | 3/2004 | Mandrusov et al. | |
| 6,706,034 B1 | 3/2004 | Bhat | |
| 6,726,677 B1 | 4/2004 | Flaherty et al. | |
| 6,726,923 B2 | 4/2004 | Iyer et al. | |
| 6,737,072 B1 | 5/2004 | Angele et al. | |
| 6,748,258 B1 | 6/2004 | Mueller et al. | |
| 6,749,617 B1 | 6/2004 | Palasis et al. | |
| 6,759,431 B2 | 7/2004 | Hunter et al. | |
| 6,761,887 B1 | 7/2004 | Kavalkovich et al. | |
| 6,777,000 B2 | 8/2004 | Ni et al. | |
| 6,777,231 B1 | 8/2004 | Katz et al. | |
| 6,790,455 B2 | 9/2004 | Chu et al. | |
| 6,824,791 B2 | 11/2004 | Mathiowitz et al. | |
| 6,858,229 B1 | 2/2005 | Hubbell et al. | |
| 6,893,431 B2 | 5/2005 | Naimark et al. | |
| 6,916,488 B1 | 7/2005 | Meier et al. | |
| 6,916,648 B2 | 7/2005 | Goddard et al. | |
| 6,926,692 B2 | 8/2005 | Katoh et al. | |
| 6,992,172 B1 | 1/2006 | Chang et al. | |
| 7,008,411 B1 * | 3/2006 | Mandrusov et al. | 604/506 |
| 7,035,092 B2 | 4/2006 | Hillman et al. | |
| 7,112,587 B2 | 9/2006 | Timmer et al. | |
| 7,129,210 B2 | 10/2006 | Lowinger et al. | |
| 7,169,127 B2 | 1/2007 | Epstein et al. | |
| 7,270,654 B2 | 9/2007 | Griego et al. | |
| 7,273,469 B1 | 9/2007 | Chan et al. | |
| 7,294,334 B1 | 11/2007 | Michal et al. | |
| 7,361,360 B2 * | 4/2008 | Kitabwalla et al. | 424/277.1 |
| 7,361,368 B2 | 4/2008 | Claude et al. | |
| 7,374,774 B2 | 5/2008 | Bowlin et al. | |
| 7,393,339 B2 | 7/2008 | Zawacki et al. | |
| 7,438,692 B2 | 10/2008 | Tsonton et al. | |
| 7,615,373 B2 | 11/2009 | Simpson et al. | |
| 7,641,643 B2 | 1/2010 | Michal et al. | |
| 7,732,190 B2 | 6/2010 | Michal et al. | |
| 7,815,590 B2 | 10/2010 | Cooper | |
| 7,854,944 B2 | 12/2010 | Mandrusov et al. | |
| 8,038,991 B1 | 10/2011 | Stankus et al. | |
| 8,187,621 B2 | 5/2012 | Michal | |
| 8,192,760 B2 | 6/2012 | Hossainy et al. | |
| 8,221,744 B2 | 7/2012 | Basu et al. | |
| 8,293,226 B1 | 10/2012 | Basu et al. | |
| 8,303,972 B2 | 11/2012 | Michal | |
| 8,383,158 B2 | 2/2013 | Michal et al. | |
| 8,388,948 B2 | 3/2013 | Basu et al. | |
| 8,486,386 B2 | 7/2013 | Michal et al. | |
| 8,486,387 B2 | 7/2013 | Michal et al. | |
| 8,500,680 B2 | 8/2013 | Claude et al. | |
| 8,521,259 B2 | 8/2013 | Mandrusov et al. | |
| 8,608,661 B1 | 12/2013 | Mandrusov et al. | |
| 8,609,126 B2 | 12/2013 | Michal et al. | |
| 2001/0023349 A1 | 9/2001 | Van Tassel et al. | |
| 2001/0055615 A1 | 12/2001 | Wallace et al. | |
| 2002/0013408 A1 | 1/2002 | Rhee et al. | |
| 2002/0042473 A1 | 4/2002 | Trollsas et al. | |
| 2002/0072706 A1 | 6/2002 | Hiblar et al. | |
| 2002/0076441 A1 | 6/2002 | Shih et al. | |
| 2002/0090725 A1 | 7/2002 | Simpson et al. | |
| 2002/0102272 A1 | 8/2002 | Rosenthal et al. | |
| 2002/0124855 A1 | 9/2002 | Chachques | |
| 2002/0131974 A1 | 9/2002 | Segal | |
| 2002/0142458 A1 | 10/2002 | Williams et al. | |
| 2002/0146557 A1 | 10/2002 | Claude et al. | |
| 2002/0151867 A1 | 10/2002 | McGuckin et al. | |
| 2002/0169420 A1 | 11/2002 | Galt et al. | |
| 2002/0188170 A1 | 12/2002 | Santamore et al. | |
| 2003/0023202 A1 | 1/2003 | Nielson | |
| 2003/0040712 A1 | 2/2003 | Ray et al. | |
| 2003/0050597 A1 | 3/2003 | Dodge et al. | |
| 2003/0078671 A1 | 4/2003 | Lesniak et al. | |
| 2003/0105493 A1 | 6/2003 | Salo | |
| 2003/0114505 A1 | 6/2003 | Nagao et al. | |
| 2003/0175410 A1 | 9/2003 | Campbell et al. | |
| 2004/0002650 A1 * | 1/2004 | Mandrusov et al. | 600/431 |
| 2004/0029268 A1 * | 2/2004 | Colb et al. | 435/325 |
| 2004/0059179 A1 * | 3/2004 | Maguire et al. | 600/16 |
| 2004/0162516 A1 * | 8/2004 | Mandrusov et al. | 604/21 |
| 2004/0181206 A1 | 9/2004 | Chiu et al. | |
| 2004/0185084 A1 | 9/2004 | Rhee et al. | |
| 2004/0208845 A1 | 10/2004 | Michal et al. | |
| 2004/0213756 A1 * | 10/2004 | Michal et al. | 424/78.17 |
| 2004/0229856 A1 | 11/2004 | Chandrasekar et al. | |
| 2005/0015048 A1 | 1/2005 | Chiu et al. | |
| 2005/0031874 A1 | 2/2005 | Michal et al. | |
| 2005/0042254 A1 | 2/2005 | Freyman et al. | |
| 2005/0064038 A1 | 3/2005 | Dinh et al. | |
| 2005/0065281 A1 | 3/2005 | Lutolf et al. | |
| 2005/0070844 A1 | 3/2005 | Chow et al. | |
| 2005/0186240 A1 | 8/2005 | Ringeisen et al. | |
| 2005/0281883 A1 | 12/2005 | Daniloff et al. | |
| 2006/0149392 A1 | 7/2006 | Hsieh et al. | |
| 2006/0233850 A1 | 10/2006 | Michal | |
| 2007/0270948 A1 | 11/2007 | Wuh | |
| 2008/0025943 A1 | 1/2008 | Michal et al. | |
| 2012/0225040 A1 | 9/2012 | Hossainy et al. | |
| 2012/0225041 A1 | 9/2012 | Hossainy et al. | |

FOREIGN PATENT DOCUMENTS

| | | |
|---|---|---|
| EP | 0861632 | 9/1998 |
| EP | 0938871 | 9/1999 |
| EP | 1 214 077 B1 | 1/2004 |
| GB | 2194144 | 3/1988 |
| JP | 61205446 | 9/1986 |
| JP | H02145600 | 6/1990 |
| JP | 06507106 | 8/1994 |
| JP | 10236984 | 9/1998 |
| JP | 3063935 | 12/1999 |
| JP | 2000502380 | 2/2000 |
| JP | 2000262525 | 9/2000 |
| JP | 2001508666 | 7/2001 |
| JP | 2001508754 | 7/2001 |

(56) References Cited

FOREIGN PATENT DOCUMENTS

| JP | 2003062089 | 3/2003 |
|---|---|---|
| JP | 2006014570 | 1/2006 |
| JP | 2006516548 | 7/2006 |
| JP | 2007009185 | 1/2007 |
| JP | 2006523507 | 10/2009 |
| WO | WO-9210142 | 6/1992 |
| WO | WO-9315781 | 8/1993 |
| WO | WO-9522316 | 8/1995 |
| WO | WO-9733633 | 9/1997 |
| WO | WO-9830207 | 7/1998 |
| WO | WO-9854301 | 12/1998 |
| WO | WO-9953943 | 10/1999 |
| WO | WO-0016818 | 3/2000 |
| WO | WO-0054661 | 9/2000 |
| WO | WO-0071196 | 11/2000 |
| WO | WO-0124775 | 4/2001 |
| WO | WO-0124842 | 4/2001 |
| WO | WO-0145548 | 6/2001 |
| WO | WO-0149357 | 7/2001 |
| WO | WO-0200173 | 1/2002 |
| WO | WO-0204008 | 1/2002 |
| WO | WO-0228450 | 4/2002 |
| WO | WO-0240070 | 5/2002 |
| WO | WO-02072166 | 9/2002 |
| WO | WO-02087623 | 11/2002 |
| WO | WO-03005961 | 1/2003 |
| WO | WO-03022324 | 3/2003 |
| WO | WO-03022909 | 3/2003 |
| WO | WO-03026492 | 4/2003 |
| WO | WO-03027234 | 4/2003 |
| WO | WO-03064637 | 8/2003 |
| WO | WO-2004000915 | 12/2003 |
| WO | WO-2004050013 | 6/2004 |
| WO | WO 2004/058305 A2 | 7/2004 |
| WO | WO-2004060346 | 7/2004 |
| WO | WO-2004066829 | 8/2004 |
| WO | WO-2004091592 | 10/2004 |
| WO | WO-2004098669 | 11/2004 |
| WO | WO-2005061019 | 7/2005 |
| WO | WO-2005067890 | 7/2005 |
| WO | WO-2006014570 | 2/2006 |
| WO | WO-2006027549 | 3/2006 |
| WO | WO-2006039704 | 4/2006 |
| WO | WO-2006113407 | 10/2006 |
| WO | WO-2007048831 | 3/2007 |
| WO | WO-2007145909 | 12/2007 |

OTHER PUBLICATIONS

Gries et al., (Cardiovascular Res. May 1, 2003;58:469-477).*
Seeger et al., (J Vasc Surg. Oct. 1988;8(4):476-82, Abstract only).*
MSDS 4-amino-2,2,6,6-tetramethlypiperidine-1-oxyl (4-amino-TEMPO) CAS No. 14691-88-4 at www.chemcas.org/drug/analytical/cas/14691-88-4.asp (first published Sep. 2, 1997; revised Aug. 8, 2007; last visited Dec. 2, 2013). 5 pages.*
Bull, S., et al., "Self-Assembled Peptide Amphiphile Nanofibers Conjugated to MRI Contrast Agents," Nano Letters, vol. 5, No. 1 (Jan. 2005) 4 pages.
Hartgerink, J.D., et al., "Peptide-amphiphile nanofibers: A versatile scaffold for the preparation of self-assembling materials," PNAS, vol. 99, No. 8 (Apr. 16, 2002) pp. 5133-5138.
Hartgerink, J.D., et al., "Self-Assembly and Mineralization of Peptide-Amphiphile Nanofibers," Science, vol. 294 (Nov. 23, 2001) pp. 1684-1688.
Li, B., et al., "VEGF and PlGF promote adult vasculogenesis by enhancing EPC recruitment and vessel formation at the site of tumor neovascularization," The FASEB Journal, vol. 20 (2006) pp. 1495-1497.
Urbich, C. and S. Dimmeler, "Endothelial Progenitor Cells: Characterization and Role in Vascular Biology," Circulation Research, vol. 95 (2004) pp. 343-353.
Yamamoto, N., et al., "Histologic evidence that basic fibroblast growth factor enhances the angiogenic effects of transmyocardial laser revascularization", Basic Research in Cardiology, vol. 95, No. 1, (Feb. 1, 2000), 55-63.
Abbott Cardiovascular Systems, Office Action dated Apr. 6, 2009 for U.S. Appl. No. 11/447,340.
Abbott Cardiovascular Systems, Office Action dated Mar. 30, 2009 for U.S. Appl. No. 10/792,960.
Abbott Cardiovascular Systems, Office Action dated Apr. 13, 2009 for U.S. Appl. No. 11/566,643.
Abbott Cardiovascular Systems, Office Action dated Apr. 29, 2009 for U.S. Appl. No. 12/013,286.
Abbott Cardiovascular Systems, Office Action dated May 12, 2009 for U.S. Appl. No. 11/496,824.
Abbott Cardiovascular Systems, Non-Final Office Action dated Mar. 13, 2009 for U.S. Appl. No. 10/414,602.
Abbott Cardiovascular Systems, International search report and written opinion dated Jun. 18, 2009 for PCT/US2008/051505.
Abbott Cardiovascular Systems, Non final office action dated Jul. 9, 2009 for U.S. Appl. No. 11/561,328.
Abbott Cardiovascular Systems, Non final office action dated Aug. 5, 2009 for U.S. Appl. No. 11/031,608.
Abbott Cardiovascular Systems, International Preliminary Report on Patentability dated Jul. 30, 2009 for PCT/US2008/051505.
Abbott Cardiovascular Systems, Final office action dated Nov. 12, 2009 for U.S. Appl. No. 12/013,286.
Abbott Cardiovascular Systems, Final office action dated Nov. 25, 2009 for U.S. Appl. No. 11/566,643.
Abbott Cardiovascular Systems, Non final office action dated Dec. 9, 2009 for U.S. Appl. No. 10/781,984.
Abbott Cardiovascular Systems, Examination Report dated Jan. 13, 2010 for EP Application No. 07795729.8.
Abbott Cardiovascular Systems, Non final office action dated Feb. 5, 2010 for U.S. Appl. No. 11/447,340.
Abbott Cardiovascular Systems, Final Office Action dated Jan. 29, 2010 for U.S. Appl. No. 10/792,960.
Abbott Cardiovascular Systems, Examination Report dated Jan. 15, 2010 for EP 08727952.7.
Abbott Cardiovascular Systems, Examination Report dated Feb. 5, 2010 for EP 07810637.4.
Abbott Cardiovascular Systems, Final office action dated Mar. 29, 2010 for U.S. Appl. No. 11/031,608.
Abbott Cardiovascular Systems, Non final office action dated Apr. 29, 2010 for U.S. Appl. No. 10/792,960.
Abbott Cardiovascular Systems, Non-Final Office Action dated Jun. 4, 2010 for U.S. Appl. No. 10/781,984.
Abbott Cardiovascular Systems, Final Office Action dated Jun. 11, 2010 for U.S. Appl. No. 11/561,328.
Abbott Cardiovascular Systems, Non final office action dated Aug. 13, 2010 for U.S. Appl. No. 11/447,340.
Abbott Cardiovascular Systems, Final office action mailed Sep. 27, 2010 for U.S. Appl. No. 10/792,960.
Abbott Cardiovascular Systems, Final office action mailed Sep. 27, 2010 for U.S. Appl. No. 12/016,180.
Abbott Cardiovascular Systems, Final Office Action mailed Nov. 22, 2010 for U.S. Appl. No. 10/781,984, 13 pages.
Abbott Cardiovascular Systems, Non-final Office Action mailed Nov. 24, 2010 for U.S. Appl. No. 12/013,286.
Abbott Cardiovascular Systems, Non-final Office Action mailed Dec. 8, 2010 for U.S. Appl. No. 11/566,643.
Abbott Cardiovascular Systems, Non-final Office Action mailed Dec. 10, 2010 for U.S. Appl. No. 11/938,752.
Abbott Cardiovascular Systems, Non-final Office Action mailed Dec. 17, 2010 for U.S. Appl. No. 11/933,922.
Abbott Cardiovascular Systems, website for HEALON (R) OVD, copyright 2010, accessed Dec. 15, 2010, URL: <http://abbottmedicaloptics.com/products/cataract/vds/healon-viscoelastic>, (2010), 2 pages.
Abbott Cardiovascular Systems, Product Information Sheet for HEALON (R), from Abbott Medical Optics, (2005), 1 page.
Abbott Cardiovascular Systems, Non final office action dated Apr. 14, 2010 for U.S. Appl. No. 12/016,180.
Abbott Cardiovascular Systems, Final office action dated Apr. 22, 2010 for U.S. Appl. No. 10/414,602.

(56) References Cited

OTHER PUBLICATIONS

Abbott Cardiovascular Systems, Japanese Office Action dated Dec. 8, 2010 for Japanese Patent App No. 2006-509975., 6 pages.
Abbott Cardiovascular Systems, Non final office action mailed Feb. 8, 2011 for U.S. Appl. No. 10/792,960.
Abbott Cardiovascular Systems, Final Office Action mailed 4/15/20 for U.S. Appl. No. 10/414,602.
Abbott Cardiovascular Systems, Non final office action mailed Jun. 7, 2011 for U.S. Appl. No. 11/447,340.
Abbott Cardiovascular Systems, Non final office action mailed Jul. 6, 2011 for U.S. Appl. No. 10/781,984.
Abbott Cardiovascular Systems, Final office action mailed Jun. 28, 2011 for U.S. Appl. No. 10/792,960.
Abbott Cardiovascular Systems, Final office action mailed Jul. 18, 2011 for U.S. Appl. No. 11/566,643.
Abbott Cardiovascular Systems, Non-Final Office Action mailed 8/31/20 for U.S. Appl. No. 11/110,223, 11 pages.
Abbott Cardiovascular Systems, Final office action mailed Sep. 20, 2011 for U.S. Appl. No. 11/938,752.
Abbott Cardiovascular Systems, Final Office Action mailed Oct. 21, 2011 for U.S. Appl. No. 10/781,984.
Abbott Cardiovascular Systems, Non final office action mailed Nov. 8, 2011 for U.S. Appl. No. 10/792,960.
Abbott Cardiovascular Systems, Final Office Action mailed 12/13/20 for U.S. Appl. No. 12/963,397.
Abbott Cardiovascular Systems, Final Office Action mailed Jan. 5, 2012 for U.S. Appl. No. 11/361,920.
Abbott Cardiovascular Systems, Office Action mailed Jan. 17, 2012 for European Patent Application 08727952.7, 6 pages.
Abbott Cardiovascular Systems, Non-Final Office Action mailed Jan. 30, 2012 for U.S. Appl. No. 10/781,984.
Abbott Cardiovascular Systems, Final Office Action mailed Feb. 8, 2012 for Japanese application No. 2006-509975, 6 pages.
Abbott Cardiovascular Systems, Non-Final Office Action mailed Feb. 15, 2012 for U.S. Appl. No. 12/114,717.
Abbott Cardiovascular Systems, Final Office Action mailed Apr. 4, 2012 for U.S. Appl. No. 10/792,960.
Abbott Cardiovascular Systems, European Office Action mailed Apr. 11, 2012 for App No. 12155231.9, 9 pages.
Abbott Cardiovascular Systems, European Office Action mailed Apr. 10, 2012 for App No. 07810637.4.
Abbott Cardiovascular Systems, Final Office Action mailed May 9, 2012or U.S. Appl. No. 11/110,223.
Abbott Cardiovascular Systems, European Search report for application No. 12151788.2 mailed Apr. 18, 2012, 6 pages.
Abbott Cardiovascular Systems, Non-final Office Action mailed Jun. 22, 2012or U.S. Appl. No. 12/963,397, 10 pages.
Abbott Cardiovascular Systems, Restriction requirement mailed Jul. 3, 2012or U.S. Appl. No. 13/472,324, 8 pages.
Abbott Cardiovascular Systems, Non-final Office Action mailed Jun. 26, 2012or U.S. Appl. No. 12/632,612., 8 pages.
Abbott Cardiovascular Systems, Japanese Office Action dated Jun. 11, 2012 for Appln. No. 2010-162711.
Abbott Cardiovascular Systems, Non-final Office Action mailed Aug. 28, 2012or U.S. Appl. No. 13/472,324.
Abbott Cardiovascular Systems, Non-final Office Action mailed Aug. 30, 2012 for U.S. Appl. No. 13/472,328.
Abbott Cardiovascular Systems, Non-Final Office Action Sep. 11, 2012 for U.S. Appl. No. 10/792,960.
Abbott Cardiovascular Systems, Japanese office action dated Aug. 20, 2012 for JP 2009-537153.
Abbott Cardiovascular Systems, Non-Final Office Action dated Oct. 3, 2012 for U.S. Appl. No. 12/756,119.
Abbott Cardiovascular Systems, et al., Japanese Office Action dated Aug. 27, 2012 for JP 2009-522776.
Abbott Cardiovascular Systems, Final Office Action dated Nov. 8, 2012 for U.S. Appl. No. 12/114,717.
Abbott Cardiovascular Systems, Final Office Action mailed Nov. 7, 2012 for U.S. Appl. No. 10/781,984.
Abbott Cardiovascular Systems, Japanese Office Action dated Nov. 19, 2012 for Appln. No. 2009-539265.
Abbott Cardiovascular Systems, Final office action dated Jan. 18, 2013 for U.S. Appl. No. 12/963,397.
Abbott Cardiovascular Systems, Japanese office action dated Oct. 9, 2012 for JP Appln. No. 2009-514330.
Abbott Cardiovascular Systems, Japanese Office Action mailed Dec. 17, 2012 for JP Appln. No. 2009-546553.
Abbott Cardiovascular Systems, Examination Report dated Feb. 20, 2013 for European Appln. No. 12151788.2, 4 pages.
Abbott Cardiovascular Systems, Non final office action dated Apr. 1, 2013 for U.S. Appl. No. 13/559,423.
Abbott Cardiovascular Systems, Non-Final Office Action dated Oct. 3, 2012 for U.S. Appl. No. 12/756,092.
Abbott Cardiovascular Systems, Final office action mailed Apr. 22, 2013 for U.S. Appl. No. 10/792,960.
Abbott Cardiovascular Systems, Japanese office action mailed Mar. 25, 2013 for JP 2009-539265.
Abbott Cardiovascular Systems in, PCT International Preliminary Report on Patentability and Written Opinion dated Dec. 24, 2008 for PCT/US2007/013181., P4437X2PCT.
Abbott Cardiovascular Systems in, PCT Search Report and Written Opinion dated Aug. 26, 2008 for PCT/US2007/016433.
Abbott Cardiovascular Systems in, PCT Search Report and Written Opinion dated Jul. 31, 2008 for PCT/US2007/024158.
Abbott Cardiovascular Systems in, "PCT International Search Report and Written Opinion mailed Feb. 10, 2009", PCT/US2007/023419.
Abbott Cardiovascular Systems in, "PCT Search Report dated Feb. 12, 2008", PCT Appln No. PCT/US2007/013181, 17.
Abbott Cardiovascular Systems in, "PCT Search Report dated Jan. 31, 2007", PCT Appln No. PCT/US2006/014021, 11 pages.
Abbott Cardiovascular Systems in, "PCT Search Report dated Mar. 27, 2008", PCT Appln No. PCT/US2007/003614, 18 pages.
Advanced Cardiovascular Systems, Extended EP Search Report dated May 20, 2011 for EP Application No. 10186197.9.
Advanced Cardiovascular Systems, Extended European search report dated Apr. 21, 2011 for EP Application No. 10186186.2.
Advanced Cardiovascular Systems, Inc., et al., "PCT International Preliminary Report on Patentability dated Jun. 19, 2007", PCT Appln. No. PCT/US2005/045627.
Advanced Cardiovascular Systems, Inc., "PCT International Preliminary Report on Patentability dated Nov. 3, 2005", PCT Appln. No. PCT/US2004/011356, 6 pages.
Advanced Cardiovascular Systems, Inc., "PCT International Search Report and Written Opinion mailed Oct. 13, 2006", PCT Appln No. PCT/US2005/045627.
Advanced Cardiovascular Systems, Inc., "PCT International Search Report dated Feb. 9, 2004", PCT Appln. No. PCT/US03/30464, 5 pages.
Advanced Cardiovascular Systems, Inc., "PCT International Search Report dated Jan. 28, 2004", PCT Appln. No. PCT/US03/18360, 7 pages.
Advanced Cardiovascular Systems, Inc., "PCT Invitation to Pay Additional Fees mailed Nov. 4, 2003", PCT Appln No. PCT/US03/18360, 3 pages.
Advanced Cardiovascular Systems, Inc., "PCT Search Report and Written Opinion dated Nov. 24, 2004", PCT Appln. No. PCT/US03/18360, 3 pages.
Agocha, A., et al., "Hypoxia regulates basal and induced DNA synthesis and collagen type I production in human cardiac fibroblasts: effects of transforming growth factor-beta 1, thyroid hormone, angiotensin II and basic fibroblast growth factor", J. Mol. Cell. Cardiol., 29(8), (Apr. 1997), pp. 2233-2244.
Allemann, E., et al., "Kinetics of Blood Component Adsorption on poly(D,L-lactic acid) Nanoparticles: Evidence of Complement C3 Component Involvement", J. Biomed. Mater. Res., 37(2), Abstract downloaded from the Internet at www.ncbi.nlm.nih.gov/entrez/query.fcgi?cmd=Retrieve&db=PubMed, (Nov. 1997), 229-234.
Anderson, James M., et al., "Biodegradation and biocompatibility of PLA and PLGA microspheres", Advanced Drug Delivery Reviews 28, (1997), 5-24.

(56) References Cited

OTHER PUBLICATIONS

Assmus, B., et al., "Transplantation of Progenitor Cells and Regeneration Enhancement in Acute Myocardial Infarction (TOPCARE-AMI)", Clinical Investigation and Reports, Circulation, 106, (2002), 3009-3017.

Baxter Healthcare Corporation, "FloSeal Matrix Hemostatic Sealant", fusionmed.com/docs/surgeon/default.asp, (2002), pp. 1-2.

Berger, et al., "Poly-L-cysteine", J. Am. Chem. Soc., 78(17), (Sep. 5, 1956), pp. 4483-4488.

Bernatowicz, M., et al., "Preparation of Boc[S-(3-nitro-2-pyridinesulfenyl)]-cysteine and its use for Unsymmetrical Disulfide Bond Formation", Int. J. Peptide Protein Res. 28(2), (Aug. 1996), pp. 107-112.

Boland, E. D., "Electrospinning Collagen and Elastin: Preliminary Vascular Tissue Engineering", Frontiers in Bioscience, vol. 9, (May 1, 2004), pp. 1422-1432.

Brust, G., "Polyimides", Department of Polymer Science; The University of Southern Mississippi, pslc.usm.edu/macrog/imide.htm, (2005), pp. 1-4.

Buschmann, I, et al., "Arteriogenesis versus angiogenesis: Two mechanisms of vessel growth", News Physiol. Sci., vol. 14, (Jun. 1999), 121-125.

Canderm Pharma, "Technical Dossier: Artecoll", downloaded from the Internet on Oct. 22, 2002 from: www.canderm.com/artecoll/tech.html, pp. 1-3.

Capan, Y., et al., "Preparation and Characterization of Poly(D,L-lactide-co-glycolide) Microspheres for Controlled Release of Human Growth Hormone", AAPS PharmSciTech., 4(2) Article 28, (2003), 1-10.

Caplan, Michael J., et al., "Dependence on pH of polarized sorting of secreted proteins", Nature, vol. 29, (Oct. 15, 1987), 630.

Carpino, L., et al., "Tris(2-aminoethyl)amine as a Substitute for 4-(Aminomethyl)piperidine in the FMOC/Polyamine Approach to Rapid Peptide Synthesis", J. Org. Chem., 55(5), (Mar. 1990), pp. 1673-1675.

Chandy, et al., "The development of porous alginate/elastin/PEG composite matrix for cardiovascular engineering", Journal of Biomaterials Applications, vol. 17, (Apr. 2003), 287-301.

Choi, Young Seon, et al., "Study on gelatin-containing artificial skin: I. Preparation and characteristics of novel gelatin-alginate sponge", Biomaterials, vol. 20, (1999), 409-417.

Chung, Y., et al., "Sol-gel transition temperature of PLGA-g-PEG aqueous solutions", Biomacromolecules, vol. 3, No. 3, (May 2002), 511-516.

Corbett, S., et al., "Covalent Cross-linking of Fibronectin to Fibrin is Required for Maximal Cell Adhesion to a Fibronectin-Fibrin Matrix", The Journal of Biological Chemistry, 272(40), (Oct. 3, 1997), pp. 24999-25005.

Creemers, E., et al., "Matrix Metalloproteinase Inhibition After Myocardial Infarction: A New Approach to Prevent Heart Failure?", Circ. Res., vol. 89, (2001), pp. 201-210.

Crivello, et al., "Synthesis and Photoinitiated Cationic Polymerization of Monomers with the Silsesquioxane Core", J Polym Science: Part A: Polymer Chemistry 35, (1997), pp. 407-425.

Davis, M. E., et al., "Injectable Self-Assembling Peptide Nanofibers Create Intramyocardial Microenvironments for Endothelial Cells", Circulation, 111, (Feb. 2005), pp. 442-450.

Davis, M E., et al., "Injectable Self-Assembling Peptide Nanofibers Create Intramyocardial Microenvironments for Endothelial Cells", Circulation, 111, (2005), 442-450.

De Rosa, et al., "Biodegradable Microparticles for the Controlled Delivery of Oligonucleotides", International Journal of Pharmaceutics, 242, (Aug. 21, 2002), pp. 225-228.

Desai, M., et al., "Polymer bound EDC (P-EDC): A convenient reagent for formation of an amide bond", Tetrahedron Letters, 34(48), Abstract downloaded from the Internet at sciencedirect.com, (Nov. 1993), 7685-7688.

Dinbergs, et al., "Cellular response to transforming growth factor-β1 and basic fibroblast growth factor depends on release kinetics and extracellular matrix interactions", The Journal of Biological Chemistry, vol. 271, No. 47, (Nov. 1996), 29822-29829.

Dong, Zhanfeng, et al., "Alginate/gelatin blend films and their properties for drug controlled release", Journal of Membrane Science, vol. 280, (2006), 37-44.

Edelman, "Controlled and modulated release of basic fibroblast growth factor", Biomaterials, vol. 12, (Sep. 1999), 619-626.

Elbert, D. L., et al., "Protein delivery from materials formed by self-selective conjugate addition reactions", Journal of Controlled Release, 76, (2001), 11-25.

Etzion, S., et al., "Influence of Embryonic Cardiomyocyte Transplantation on the Progression of Heart Failure in a Rat Model of Extensive Myocardial Infarction", J. Mol. Cell Cardiol., 33, (May 2001), pp. 1321-1330.

Ferrara, N., "Role of Vascular Endothelial Growth Factor in the Regulation of Angiogenesis", Kidney International, 56(3), Abstract downloaded from the Internet at nature.com/ki/journal/v56/n3/abs/4490967a.html, (1999), 794-814.

Friedman, Paul M., et al., "Safety Data of Injectable Nonanimal Stabilized Hyaluronic Acid Gel for Soft Tissue Augmentation", Dermatologic Surgery, vol. 28, (2002), pp. 491-494.

Fuchs, S., et al., "Catheter-Based Autologous Bone Marrow Myocardial Injection in No-Option Patients with Advanced Coronary Artery Disease", J. Am. Coll. Cardiol., 41(10), (2003), pp. 1721-1724.

Fukumoto, S., et al., "Protein Kinase C δ Inhibits the Proliferation of Vascular Smooth Muscle Cells by Suppressing G1 Cyclin Expression", The Journal of Biological Chemistry, 272(21), (May 1997), pp. 13816-13822.

Giordano, F., et al., "Angiogenesis: The Role of the Microenvironment in Flipping the Switch", Current Opinion in Genetics and Development, 11, (2001), pp. 35-40.

Gossler, et al., "Transgenesis by means of blastocyst-derived embryonic stem cell lines", Proc. Natl. Acad. Sci. USA, 83, (Dec. 1986), pp. 9065-9069.

Grafe, T. H., "Nanofiber Webs from Electrospinning", Presented at the Nonwovens in Filtration—Fifth International Conference Stuttgart, Germany, (Mar. 2003), pp. 1-5.

Gref, R., et al., "Biodegradable Long-Circulating Polymeric Nanospheres", Science, 263(5153), Abstract downloaded from the Internet at: www.sciencemag.org/cgi/content/abstract/263/5153/1600, 1 page, (Mar. 1994).

Grund, F., et al., "Microembolization in Pigs: Effects on Coronary Blood Flow and Myocardial Ischemic Tolerance", Am. J. Physiol., 277 (Heart Circ. Physiol. 46), (1999), pp. H533-H542.

Gupta, et al., "Changes in Passive Mechanical Stiffness of Myocardial Tissue with Aneurysm Formation", Circulation, 89(5), (May 1994), pp. 2315-2326.

Hanawa, T., et al., "New oral dosage form for elderly patients: preparation and characterization of silk fibroin gel", Chemical and Pharmaceutical Bulletin, Pharmaceutical Society of Japan, Tokyo, vol. 43, No. 2, (Jan. 1995), 284-288.

Hao, X, et al., "Angiogenic Effects of Sequential release of VEGF-A 165 and PDGF-BB with Alginate Hydrogels After Myocardial Infarction", Cardiovascular Research, 75(1), (Apr. 6, 2007), 178-185.

Hao, X, et al., "Angiogenic effects of sequential release of VEGF-A165 and PDGF-BB with alginate hydrogels after myocardial infarction", Cardiovascular Research, 75, (2007), 178-185.

Hashimoto, T., et al., "Development of Alginate Wound Dressings Linked with Hybrid Peptides Derived from Laminin and Elastin", Biomaterials, 25, (2004), pp. 1407-1414.

Haugland, et al., "Dialkylcarbocyanine and Dialkylaminostryryl Probes", Handbook of Fluorescent Probes and Research Products, Molecular Probes, Inc., (2002), 530-534.

Haugland, et al., "Membrane-permeant reactive tracers", Handbook of Fluorescent Probes and Research Products, Molecular Probes, Inc., (2002), 458-553.

Haynesworth, Stephen E., et al., "Platelet Effects on Human Mesenchymal Stem Cells", Abstract, presented at Orthopaedic Research Society 48th Annual Meeting, Dallas, TX, (Feb. 10-13, 2010), 2 pages.

(56) References Cited

OTHER PUBLICATIONS

Heeschen, C., et al., "Nicotine Stimulates Tumor Angiogenesis", American College of Cardiology, 37(2) Supplement A Abstract downloaded from the Internet at: 24.132.160.238/ciw-01acc/abstract_search_author.cfm?SearchName=Heeschen, 1 page, (Feb. 2001), pp. 1A-648A.

Helisch, A, et al., "Angiogenesis and arteriogenesis", NEUE Diagnostische Und Therap. Verfahren, Z Kardiol 89, (2000), 239-244.

Hendel, R. C., et al., "Effect of Intracoronary Recombinant Human Vascular Endothelial Growth Factor on Myocardial Perfusion: Evidence for a Dose-Dependent Effect", Circulation, 101, (2000), pp. 118-121.

Henry, R. R., et al., "Insulin Action and Glucose Metabolism in Nondiabetic Control and NIDDM Subjects: Comparison Using Human Skeletal Muscle Cell Cultures", Diabetes, 44(8), Abstract downloaded from the Internet at www.diabetes.diabetesjournals.org/cgi/content/abstract/44/8/936, (1995), pp. 936-946.

Hoffman, "Hydrogels for Biomedical Applications", Advanced Drug Delivery Reviews, vol. 43, (2002), pp. 3-12.

Holland, N. B., et al., "Biomimetic Engineering of Non-Adhesive glycocalyx-like Surfaces Using Oligosaccharide Surfactant Polymers", Nature, 392, Abstract downloaded from the Internet at www.nature.com, (Apr. 1998), pp. 799-801.

Horan, R.L., et al., "In Vitro Degradation of Silk Fibroin", Biomaterials, vol. 26, (2004), 3385-3393.

Hovinen, J., et al., "Synthesis of 3'-functionalized oligonucleotides on a single solid support", Tetrahedron Letters, 34(50), Abstract downloaded from the Internet at www.sciencedirect.com, (Dec. 1993), pp. 8169-8172.

Huang, K., et al., "Synthesis and Characterization of Self-Assembling Block Copolymers Containing Bioadhesive End Groups", Biomacromolecules, 3(2), (2002), pp. 397-406.

Hutcheson, K., et al., "Comparison of Benefits on Myocardial Performance of Cellular Cardiomyoplasty with Skeletal Myoblasts and Fibroblasts", Cell Transplantation, 9(3), (2000), pp. 359-368.

Huynh, T. V., et al., "Constructing and Screening cDNA Libraries in λgt10 and λgt11", Chapter 2 in DNA Cloning, vol. 1: A Practical Approach, ed. by D.M. Glover, (1985), pp. 49-78.

Indik, Z., et al., "Production of Recombinant Human Tropoelastin: Characterization and Demonstration of Immunologic and Chemotactic Activity", Arch. Biochem. Biophys., 280(1), Abstract downloaded from the Internet at: www.ncbi.nlm.nih.gov/ ntrez/query.fcgi?cmd=Retrieve&db=PubMed, 1 page, (Jul. 1990), pp. 80-86.

Iskandrian, A. S., et al., "Nuclear Cardiac Imaging: Principles and Applications", second edition, F.A. Davis Co., Philadelphia, cover page, title page and TOC, (1996), 5 pages total.

Isner, J. M., "Vascular Endothelial Growth Factor: Gene Therapy and Therapeutic Angiogenesis", Am. J. Cardiol., 82(10A), (Nov. 19, 1998), pp. 63S-64S.

Ito, Wulf D., et al., "Monocyte chemotactic protein-1 increases collateral and peripheral conductance after femoral artery occlusion", Max-Planck-Institute for Physiological and Clinical Research, Bad Nauheim, Germany, (Feb. 21, 1997), 829-837.

Johnson, et al., "The stabilization and encapsulation of human growth hormone nto biodegradable microspheres", Pharmaceutical Research, vol. 14, No. 6, (1997), 730-735.

Jonasson, P., et al., "Denatured states of human carbonic anhydrase II: an NMR study of hydrogen/deuterium exchange at tryptophan-indole-Hn sites", FEBS Letters, 445, (1999), pp. 361-365.

Kalltorp, Mia, et al., "Inflammatory cell recruitment, distribution, and chemiluminescence response at IgG precoated- and thiol functionalized gold surfaces", Swedish Biomaterials Consortium, Swedish Foundation for Strategic Research, (Apr. 9, 1999), 251-259.

Kaplan, D.L., et al., "Spiderless Spider Webs", Nature Biotechnology, vol. 20, (2002), 239-240.

Kawai, et al., "Accelerated tissue regeneration through incorporation of basic fibroblast growth factor-impregnated gelatin microspheres into artificial dermis", Biomaterials, 21(5), (Mar. 2000), 489-499.

Kawasuji, M., et al., "Therapeutic Angiogenesis with Intramyocardial Administration of Basic Fibroblast Growth Factor", Ann Thorac Surg, 69, Abstract downloaded from the Internet at www.ats.ctsnetjournals.org/cgi/content/abstract/69/4/1155, (2000), pp. 1155-1161.

Kelley, et al., "Restraining Infarct Expansion Preserves Left Ventricular Geometry and Function After Acute Anteroapical Infarction", Circulation, 99, (1999), pp. 135-142.

Kelly, E. B., "Advances in Mammalian and Stem Cell Cloning", Genetic Engineering News, vol. 23, No. 7, (Apr. 1, 2003), pp. 17-18 & 68.

Khademhosseini, et al., "Microscale Technologies for Tissue Engineering and Biology", PNAS, vol. 103, No. 8, (Feb. 21, 2006), pp. 2480-2487.

Kim, D., et al., "Glow Discharge Plasma Deposition (GDPD) Technique for the Local Controlled Delivery of Hirudin from Biomaterials", Pharmaceutical Research, 15(5), (1998), pp. 783-786.

Kim, Ung-Jin, et al., "Structure and Properties of Silk Hydrogels", Biomacromolecules, vol. 5(3), (2004), 786-792.

Kinart, et al., "Electrochemical Studies of 2-hydroxy-3-(3,4-dimethyl-9-oxo-9H-thioxanthen-2-yloxy)N,N,N-trimethyl-1-1-propanium chloride", J. Electroanal. Chem, 294, (1990), pp. 293-297.

Kipshidze, Nicholas, et al., "Therapeutic angiogenesis for critical limb ischemia to limit or avoid amputation", University of Wisconsin Medical School, The Journal of Invasive Cardiology, vol. 11, No. 1, (Jan. 1999), 25-28.

Klein, S., et al., "Fibroblast Growth Factors as Angiogenesis Factors: New Insights Into Their Mechanism of Action", Regulation of Angiogenesis, I.D. Goldberg and E.M. Rosen (eds.), 79, (1997), pp. 159-192.

Klugherz, Bruce D., et al., "Gene delivery from a DNA controlled-release stent in porcine coronary arteries", Nature Biotechnology, vol. 18, (Nov. 2000), 1181-1184.

Kohilas, K, et al., "Effect of prosthetic titanium wear debris on mitogen-induced monocyte and lymphoid activation", John Hopkins University, Dept. of Orthopaedic Surgery, (Apr. 1999), 95-103.

Kweon, H. Y., et al., "Preparation of semi-interpenetrating polymer networks composed of silk fibroin and poly(ethyleneglycol) macromer", Journal of Applied Polymer Science, John Wiley and Sons Inc., New York, NY, vol. 80, (Jan. 2001), 1848-1853.

Kwok, C., et al., "Design of Infection-Resistant Antibiotic-Releasing Polymers: I. Fabrication and Formulation", Journal of Controlled Release, 62, (1999), pp. 289-299.

Laboratory of Liposome Research, "Liposomes: General Properties", downloaded from the Internet on Feb. 9, 2006 at www.unizh.ch/onkwww/lipos.htm.

Laham, R. J., "Intrapericardial Delivery of Fibroblast Growth Factor-2 Induces Neovascularization in a Porcine Model of Chronic Myocardial Ischemia", J. Pharmacol Exper Therap, 292(2), (2000), pp. 795-802.

Leibovich, S. J., et al., "Macrophage-Induced Angiogenesis is Mediated by Tumour Necrosis Factor-α", Nature, vol. 329, (Oct. 15, 1987), pp. 630-632.

Leor, J., et al., "Bioengineered Cardiac Grafts—A New Approach to Repair the Infarcted Myocardium?", Circulation, 102[suppl III], (2000), pp. III-56-III-61.

Leor, J., et al., "Gene Transfer and Cell Transplant: An Experimental Approach to Repair a 'Broken Heart'", Cardiovascular Research, 35, (1997), pp. 431-441.

Leroux, J. C., et al., "An Investigation on the Role of Plasma and Serum Opsonins on the Internalization of Biodegradable poly(D,L-lactic acid) Nanoparticles by Human Monocytes", Life Sci., 57(7), Abstract downloaded from the Internet at www.ncbi.nlm.nih.gov/entrez/query.fcgi?cmd=Retrieve&db=pubmed, (1995), pp. 695-703.

Lewin, B., "Repressor is Controlled by a Small Molecule Inducer", Genes VII, Oxford University Press, 7th ed., (2000), pp. 277-280.

Li, et al., "Cell Therapy to Repair Broken Hearts", Can. J. Cardiol., vol. 14, No. 5, (May 1998), pp. 735-744.

Li, W. W., et al., "Lessons to be Learned from Clinical Trials of Angiogenesis Modulators in Ischemic Diseases", Angiogenesis in Health & Disease: Basic Mechanisms and Clinical Applications, Rubanyi, G. (ed), Marcel Dekker, Inc. New York, (2000), Chapter 33.

(56) References Cited

OTHER PUBLICATIONS

Li, J., et al., "PR39, A Peptide Regulator of Angiogenesis", Nature Medicine, 6(1), (Jan. 2000), pp. 49-55.

Li., Y. Y., et al., "Differential Expression of Tissue Inhibitors of Metalloproteinases in the Failing Human Heart", Circulation, 98(17), (1998), pp. 1728-1734.

Lindsey, M., et al., "Selective Matrix Metalloproteinase Inhibition Reduces Left Ventricular Remodeling but does not Inhibit Angiogenesis after Myocardial Infarction", Circulation, 105(6), (2002), pp. 753-758.

Long, D. M., et al., "Self-Cleaving Catalytic RNA", FASEB Journal, 7, (1993), pp. 25-30.

Lopez, J. J., et al., "Angiogenic potential of perivascular delivered aFGF in a porcine model of chronic myocardial ischemia", The American Physiological Society, 0363-6135/98, (1998), H930-H936.

Lopez, J. J., et al., "VEGF Administration in Chronic Myocardial Ischemia in Pigs", Cardiovasc. Res., 40(2), Abstract downloaded from the Internet at: www.ncbi.nlm.nih.gov/entrez/query. fcgi?cmd=Retrieve&db=pubmed, 1 page, (1998), pp. 272-281.

Lu, L., et al., "Biodegradable Polymer Scaffolds for Cartilage Tissue Engineering", Clinical Orthopaedics and Related Research, Carl T. Brighton (ed.). No. 391S, (2001), pp. S251-270.

Luo, Y., et al., "Cross-linked Hyaluronic Acid Hydrogel Films: New Biomaterials for Drug Delivery", Journal of Controlled Release, 69, (2000), pp. 169-184.

Lutolf, M, et al., "Synthesis and Physicochemical Characterization of End-Linked Poly(ethylene glycol)-co-peptide Hydrogels Formed by Michael-Type Addition", Biomacromolecules, vol. 4, (2003), 713-722.

Lyman, M. D., et al., "Characterization of the Formation of Interfacially Photopolymerized Thin Hydrogels in Contact with Arterial Tissue", Biomaterials, 17(3), (1996), pp. 359-364.

Mansour, S., et al., "Disruption of the proto-oncogene int-2 in mouse embryo-derived stem cells: a general strategy for targeting mutations to non-selectable genes", Nature, 336, (1988), pp. 348-352.

Martin, S. L., et al., "Total Synthesis and Expression in *Escherichia coli* of a Gene Encoding Human Tropoelastin", Gene, (1995), Abstract.

McDevitt, T., et al., "In vitro Generation of Differentiated Cardiac Myofibers on Micropatterned Laminin Surfaces", J. Biomed Mater Res., 60, (2002), pp. 472-479.

Meinel, L., et al., "The Inflammatory Responses to Silk Films In Vitro and In Vivo", Biomaterials, vol. 26, (2005), 147-155.

Mogan, L., "Rationale of platelet gel to augment adaptive remodeling of the injured heart", J Extra Corpor Technol, 36(2), (Jun. 2004), 191-196.

Narmoneva, D. A., et al., "Self-assembling short oligopeptides and the promotion of angiogenesis", Biomaterials, 26, (2005), pp. 4837-4846.

Nazarov, R., et al., "Porous 3-D Scaffolds from Regenerated Silk Fibroin", Biomacromolecules, vol. 5(3), (2004), 718-726.

Nguyen, K. T., et al., "Photopolymerizable Hydrogels for Tissue Engineering Applications", Biomaterials, 23, (2002), pp. 4307-4314.

Nikolic, S. D., et al., "New Angiogenic Implant Therapy Improves Function of the Ischemic Left Venticle", Supplement to Circulation; Abstracts From Scientific Sessions 2000, 102(18), (Oct. 2000), pp. II-689, Abstract 3331.

Nikolic, Serjan D., et al., "Novel means to improve coronary blood flow", Clinical Science, Abstracts from Scientific Sessions, (2000), II-689.

Nitinol Technical Information, "NiTi Smart Sheets", downloaded from the Internet on Dec. 10, 2002 at: www.sma-inc.com/information.html, 1 page.

Nose, et al., "A novel cadherin cell adhesion molecule: its expression patterns associated with implantation and organogenesis of mouse embryos", Journal of Cell Biology, vol. 103 (No. 6, Pt. 2), The Rockefeller University Press, (Dec. 1986), 2649-2658.

Ohyanagi, H., et al., "Kinetic Studies of Oxygen and Carbon Dioxide Transport into or from Perfluorochemical Particles", Proc. ISAO, vol. 1 (Artificial Organs vol. 2 (Suppl.)), (1977), pp. 90-92.

Ozbas, B., et al., "Salt-Triggered Peptide Folding and Consequent Self-Assembly into Hydrogels with Tunable Modulus", Macromolecules, 37(19), (2004), pp. 7331-7337.

Ozbas-Turan, S., "Controlled Release of Interleukin-2 from Chitosan Microspheres", Journal of Pharmaceutical Sciences, 91(5), (May 2002), pp. 1245-1251.

Palmiter, R., et al., "Germ-Line Transformation of Mice", Ann. Rev. Genet., 20, (1986), pp. 465-499.

Patrick, C. R., "Mixing and Solution Properties of Organofluorine Compounds", Preparation, Properties and Industrial Applications of Organofluorine Compounds, Chapter 10, R.E. Banks (ed.), 1st edition, Ellis-Horwood Ltd., Chichester:England, (1982), pp. 323-342.

Peattie, R. A., et al., "Stimulation of In Vivo Angiogenesis by Cytokine-Loaded Hyaluronic Acid Hydrogel Implants", Biomaterials, 25(14), Abstract downloaded from: www.sciencedirect.com, (Jun. 2004).

Penta, K., et al., "Dell Induces Integrin Signaling and Angiogenesis by Ligation of $\alpha V \beta 3$", J. Biolog. Chem., 274(16), (Apr. 1999), pp. 11101-11109.

Perin, E. C., et al., "Transendocardial, Autologous Bone Marrow Cell Transplantation for Severe, Chronic, Ischemic Heart Failure", Circulation, (2003).

Pouzet, B., et al., "Is Skeletal Myoblast Transplantation Clinically Relevant in the Era of Angiotensin-Converting Enzyme Inhibitors?", Circulation, 104 [suppl I], (Sep. 2001), pp. I-223-I-228.

Prather, et al., "Nuclear Transplantation in Early Pig Embryos", Biol. Reprod., 41, (1989), pp. 414-418.

Quellec, P., et al., "Protein Encapsulation Within Polyethylene Glycol-coated Nanospheres. I. Physicochemical Characterization", J. Biomed. Mater. Res., 42(1), (1998)), Abstract.

Ramirez-Solis, R., et al., "Gene Targeting in Embryonic Stem Cells", Methods in Enzymology, 225, (1993), pp. 855-878.

Ritter, A. B., et al., "Elastic modulus, distensibility, and compliance (capacitance)", Biomedical Engineering Principles, Chapter 4, (2005), 187-191.

Rowley, et al., "Alginate Hydrogels as Synthetic Extracelllular Matrix Materials", Biomaterials, 20(1), (1999), 45-53.

Sawhney, A. S., et al., "Bioerodible Hydrogels Based on Photopolymerized Poly(ethylene glycol)-co-poly(a-hydroxy acid) Diacrylate Macromers", Macromolecules, 26(4), (1993), pp. 581-587.

Sbaa-Ketata, E., et al., "Hyaluronan-Derived Oligosaccharides Enhance SDF-1-Dependent Chemotactic Effect on Peripheral Blood Hematopoietic CD34+ Cells", Stem Cells, 20(6), Letter to the Editor downloaded from the Internet at www.stemcells.alphamedpress.org/cgi/content/full/20/6/585, (2002), 585-587.

Segura, T, et al., "Crosslinked Hyaluronic Acid Hydrogels: A Strategy to Functionalize and Pattern", Biomaterials, vol. 26(4), (Feb. 2005), 359-371.

Segura, T, et al., "DNA delivery from hyaluronic acid-collagen hydrogels via a substrate-mediated approach", Biomaterials, vol. 26, (2005), 1575-1584.

Segura, T., et al., "Substrate-Mediated DNA Delivery: Role of the Cationic Polymer Structure and Extent of Modification", Journal of Controlled Release, 93, (2003), pp. 69-84.

Segura, T., et al., "Surface-Tethered DNA Complexes for Enhanced Gene Delivery", Bioconjugate Chem, 13(3), (2002), pp. 621-629.

Shibasaki, F., et al., "Suppression of Signalling Through Transcription Factor NF-AT by Interactions Between Calcineurin and Bcl-2", Nature, 386(6626), Abstract downloaded from the Internet at www.ncbi.nlm.nih.gov/entrez/query.fcgi?CMD=Text&DB=pubmed, (1997).

Shin, H., et al., "Attachment, Proliferation, and Migration of Marrow Stromal Osteoblasts Cultured on Biomimetic Hydrogels Modified with an Osteopontin-Derived Peptide", Biomaterials, 25, (2004), pp. 895-906.

Shin, H., et al., "In vivo bone and soft tissue response to injectable, biodegradable oligo(poly(ethylene glycol) fumarate) hydrogels", Biomaterials 24, Elseview Science Ltd., (3201-3211), 2003.

(56) References Cited

OTHER PUBLICATIONS

Shu, Z, et al., "Disulfide-crosslinked hyaluronan-gelatin hydrogel films: a covalent mimic of the extracellular matrix for in vitro cell growth", Biomaterials, vol. 24(21), (Sep. 2003), 3825-3834.

Shu, Zheng, et al., "In situ crosslinkable hyaluronan hydrogels for tissue engineering", Biomaterials, vol. 25, No. 7-8, (Mar. 2004), 1339-1348.

Simons, M., et al., "Clinical trials in coronary angiogenesis: Issues, problems, consensus, an expert panel summary", Angiogenesis Research Center, American Heart Association, Inc. (Sep. 12, 2000), 1-14.

Spenlehauer, G, et al., "In vitro and in vivo degradation of poly(D,L lactide/glycolide) type microspheres made by solvent evaporation method", Biomaterials, vol. 10, (Oct. 1989), 557-563.

Spinale, F. G., "Matrix Metalloproteinases—Regulation and Dysregulation in the Failing Heart", Circ. Res., 90, (2002), pp. 520-530.

Springer, M., et al., "Angiogenesis Monitored by Perfusion with a Space-Filling Microbead Suspension", Mol. Ther., 1(1), Abstract downloaded from the Internet at www.ncbi.nlm.nih.gov/entrez/query.fcgi?cmd=Retrieve&db=PubMed, (2000), pp. 82-87.

Staatz, WD, et al., "Identification of a tetrapeptide recognition sequence for the alpha 2 beta 1 integrin in collagen", Journal of Biological Chemistry, 1991, 266(12), pp. 7363-7367.

Storm, G., et al., "Surface Modification of Nanoparticles to Oppose Uptake by the Mononuclear Phagocyte System", Advanced Drug Delivery Reviews, 17(1), Abstract downloaded from the Internet at www.sciencedirect.com, (Oct. 1995), pp. 31-48.

Strauer, B., et al., "Repair of Infarcted Myocardium by Autologous Intracoronary Mononuclear Bone Marrow Cell Transplantation in Humans", Circulation, 106, (2002), pp. 1913-1918.

Tybulewicz, V., et al., "Neonatal lethality and lymphopenia in mice with a homozygous disruption of the c-abl proto-oncogene", Cell, 65(7), Abstract downloaded from the Internet at www.sciencedirect.com, (Jun. 1991), pp. 1153-1163.

Unger, E. F., et al., "Effects of a Single Intracoronary Injection of Basic Fibroblast Growth Factor in Stable angina Pectoris", Am. J. Cardiol, 85(12), Abstract downloaded from the Internet at www.sciencedirect.com, (Jun. 2000), pp. 1414-1419.

Van Der Giessen, Willem J., et al., "Marked inflammatory sequelae to implantation of biodegradable and nonbiodegradable polymers in porcine coronary arteries", Dept. of Cardiology, Erasmus University Rotterdam, Circulation, vol. 94, No. 7, (Oct. 1, 1996), 1690-1697.

Van Luyn, M. J., et al., "Cardiac Tissue Engineering: Characteristics of In Unison Contracting Two- and Three-Dimensional Neonatal Rat Ventricle Cell (Co)-Cultures", Biomaterials, 23, (2002), pp. 4793-4801.

Vercruysse, K. P., et al., "Synthesis and in Vitro Degradation of New Polyvalent Hydrazide Cross-Linked Hydrogels of Hyaluronic Acid", Bioconjugate Chem, 8(5), Abstract downloaded from the Internet at pubs.acs.org/cgi-bin/abstract.cgi/bcches/1997/8/i05/abs/bc9701095.html, (1997), pp. 686-694.

Visscher, G.E., et al., "Tissue response to biodegradable injectable microcapsules", Journal of Biomaterials Applications, vol. 2, (Jul. 1987), 118-119.

Vlodavsky, I., et al., "Extracellular Matrix-resident Basic Fibroblast Growth Factor: Implication for the Control of Angiogenesis", J. Cell Biochem, 45(2), Abstract downloaded from the Internet at www.ncbi.nlm.nih.gov/entrez/query.fcgi?cmd=Retrieve&db=PubMed, (Feb. 1991), pp. 167-176.

Wang, M., et al., "Mechanical Properties of Electrospun Silk Fibers", Macromolecules, vol. 37(18), (2004), 6856-6864.

Wilensky, R., et al., "Direct intraarterial wall injection of microparticles via a catheter: a potential durg delivery strategy following angioplasty", American Heart Journal, 122, (1991), p. 1136.

Witzenbichler, B., et al., "Vascular Endothelial Growth Factor-C (VEGF-C/VEGF-2) Promotes Angiogenesis in the Setting of Tissue Ischemia", Am Pathol., 153(2), (Aug. 1998), pp. 381-394.

Yager, P., et al., "Silk Protein Project", www.faculty.washington.edu/yagerp/silkprojecthome.html, (Aug. 23, 1997), pp. 1-16.

Yeo, L.Y., et al., "AC Electrospray Biomaterials Synthesis", Biomaterials, (2005), 7 pages.

Zervas, L., et al., "On Cysteine and Cystine Peptides. II. S-Acylcysteines in Peptide Synthesis", J. Am. Chem. Soc., 85(9), (May 1963), pp. 1337-1341.

Zheng, Shu, et al., "In situ crosslinkable hyaluronan hydrogels for tissue engineering", Biomaterials, Elsevier Science Publishers, vol. 25, No. 7-8, (2004), 1339-1348.

Zheng, W., "Mechanisms of coronary angiogenesis in response to stretch; role of VEGF and TGF-Beta", Am J Physiol Heart Circ Physiol 280(2), (Feb. 2001), H909-H917.

Zimmermann, W., et al., "Engineered Heart Tissue for Regeneration of Diseased Hearts", Biomaterials, 25, (2004), pp. 1639-1647.

Abbott Cardiovascular Systems, Non-Final Office Action mailed Dec. 4, 2013 for U.S. Appl. No. 11/561,328.

Abbott Cardiovascular Systems, Notice of Allowance mailed Sep. 30, 2013 for U.S. Appl. No. 13/559,423.

Abbott Cardiovascular Systems, Japanese office action mailed Nov. 22, 2013 for JP 2009-539265, (10 pages).

Abbott Cardiovascular Systems, Final Office Action mailed Feb. 4, 2014 for U.S. Appl. No. 13/888,143.

Abbott Cardiovascular Systems, Non-Final office action mailed May 31, 2013 for U.S. Appl. No. 13/559,438.

Abbott Cardiovascular Systems, Non-Final office action mailed Jul. 2, 2013 for U.S. Appl. No. 11/938,752.

Abbott Cardiovascular Systems, Non-Final office action dated Aug. 20, 2013 for U.S. Appl. No. 12/114,717.

Abbott Cardiovascular Systems, Non-Final Office Action mailed Oct. 16, 2013 for U.S. Appl. No. 13/468,956.

Abbott Cardiovascular Systems, Non-Final Office Action mailed Oct. 23, 2013 for U.S. Appl. No. 11/110,223.

Abbott Cardiovascular Systems, Notice of Allowance mailed Dec. 23, 2013 for U.S. Appl. No. 13/559,438.

Abbott Cardiovascular Systems, Final office action dated Mar. 21, 2014 for U.S. Appl. No. 12/114,717.

Abbott Cardiovascular Systems, Japanese Office Action dated Apr. 2, 2015 for JP Appln. No. 2014-076351 with English translation.

* cited by examiner

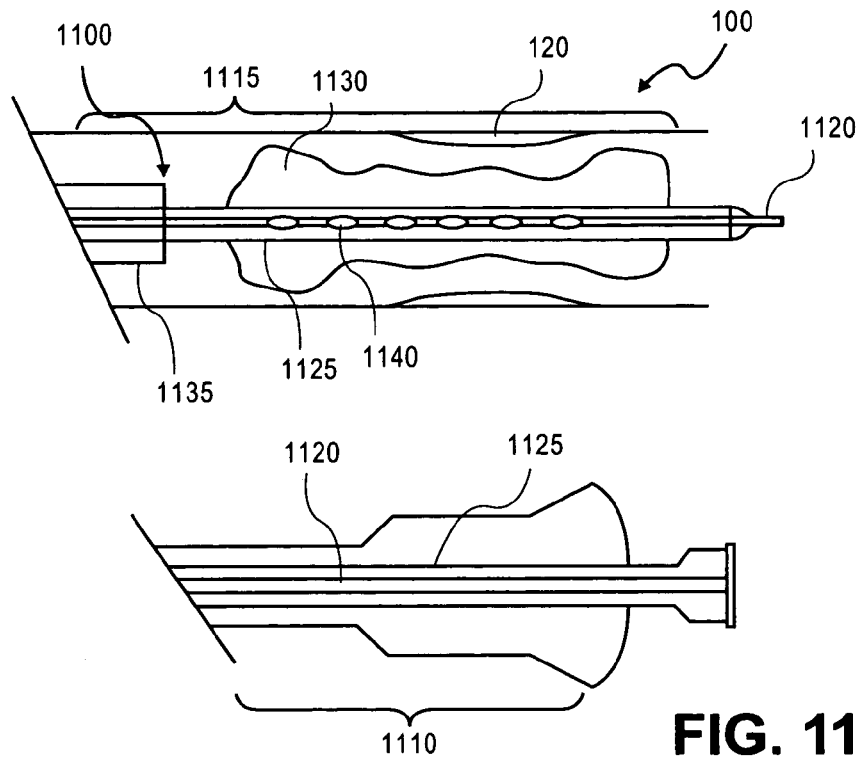
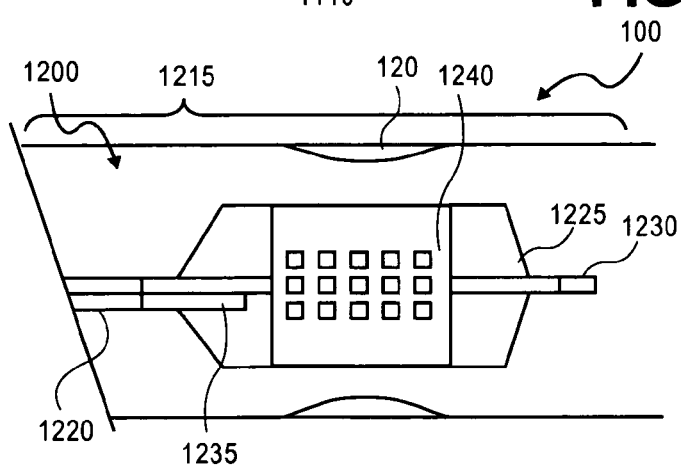
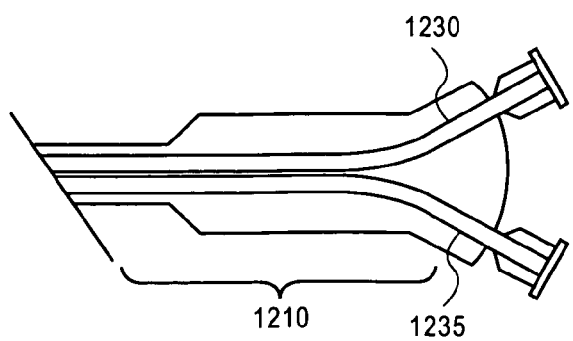
FIG. 11
FIG. 12

PRO-HEALING AGENT FORMULATION COMPOSITIONS, METHODS AND TREATMENTS

FIELD OF INVENTION

Interventional cardiology.

BACKGROUND OF INVENTION

The larger blood vessels of the body share a common anatomy. The inner lining is the endothelium, followed by subendothelial connective tissue, i.e., laminin, among other constituents, followed by a vascular smooth muscle layer. Finally, there is a connective tissue layer called the adventitia, which contains nerves that supply the muscular layer, as well as nutrient capillaries in the larger blood vessel. In contrast, smaller capillaries consist of little more than a layer of endothelium and occasional connective tissue.

The "endothelium" is a layer of thin, flat cells that lines the interior surface of blood vessels, forming an interface between circulating blood in a lumen of the blood vessel and the rest of a blood vessel wall. Endothelial cells line the entire circulatory system, include the coronary vasculature and capillaries. These cells are involved in a number of regulatory vascular processes, including, vasoconstriction and vasodilation, thrombosis and fibrinolysis, atherosclerosis, angiogenesis, and inflammation and edema. "Vasoconstriction" and "vasodilation" refer to the narrowing and widening of a blood vessel, respectively. "Thrombosis" is the formation of a clot within a blood vessel obstructing the flow of blood throughout the circulatory system. "Fibrinolysis" is the process wherein a fibrin clot formed within a blood vessel is broken down. "Angiogenesis" is the promotion or causation of new blood vessel formation. "Atherosclerosis" is a type of arteriosclerosis (thickening and hardening of arteries) in which cells including smooth muscle cells and macrophages, fatty substances, cholesterol, cellular waste product, calcium and fibrin build up on a blood vessel's inner lining.

The absence of a healthy endothelium or the presence of a diseased endothelium can lead to thrombosis or atherosclerotic plaque build-up. In some medical procedures, the endothelium can become denuded or damaged. For example, the endothelium can become denuded or damaged by an angioplasty procedure or the placement of an implantable medical device such as a stent. "Denuded" refers to the stripping of the endothelium in a blood vessel. In addition, ischemia reperfusion; a myocardial infarction; drugs which are delivered locally, regionally or systemically and which are capable of stripping the endothelium layer; and viruses or bacteria which are capable of stripping the endothelium layer can damage the endothelium. Likewise, regions of diseased vessels, such as atherosclerotic vessels, often have a dysfunctional endothelium.

Percutaneous transluminal coronary angioplasty (PTCA) is a procedure for treating heart disease, particularly stenosis. "Stenosis" refers to a narrowing or constriction of the diameter of a vessel. In a typical PTCA procedure, a catheter assembly having a balloon portion is introduced percutaneously into the cardiovascular system of a patient via the brachial or femoral artery to treat stenosis at a lesion site. The catheter assembly is advanced through the coronary vasculature until the balloon portion crosses the occlusive lesion. Once in position across the lesion, the balloon is inflated to a predetermined size to radially compress the atherosclerotic plaque of the lesion against the artery's inner wall, which dilates the lumen. The balloon is then deflated to allow the catheter to be withdrawn from the patient's vasculature.

The treatment of a diseased site or lesion within a blood vessel can involve both delivery and deployment of a stent. "Delivery" refers to introducing and transporting the stent through a blood vessel to a lesioned site that requires treatment. "Deployment" means expanding the stent within the lumen of a blood vessel at the treatment site. Delivery and deployment of a stent are accomplished by positioning the stent about one end of the catheter, percutaneously inserting the end of the catheter into the blood vessel, advancing the catheter within the lumen of the blood vessel to the treatment site, expanding the stent at the treatment site and removing the catheter from the lumen of the blood vessel. The stent can be balloon-inflatable or self-expanding.

SUMMARY OF INVENTION

Pro-healing agent formulation compositions, methods and treatments for enhancing vascular healing are disclosed herein. In some embodiments, a pro-healing agent is delivered to a denuded or damaged endothelium treatment area in a blood vessel. In some embodiments, a pro-healing agent is encapsulated, suspended, disposed within or loaded into a biodegradable carrier for sustained-release delivery to a denuded or damaged endothelium treatment area in a blood vessel. In some applications, the pro-healing agent can accelerate re-endothelialization of a denuded vascular region. In some applications, the pro-healing agent can assist in the regaining of endothelium functionality. The formulation can be delivered by a delivery assembly such as a syringe, an infusion catheter, a porous balloon catheter, a needle injection catheter, a double balloon catheter, and the like.

BRIEF DESCRIPTION OF DRAWINGS

FIG. 11 shows a blood vessel and a sixth embodiment of a catheter assembly to deliver a treatment agent introduced into the blood vessel.

FIG. 12 shows a blood vessel and a seventh embodiment of a catheter assembly to deliver a treatment agent introduced into the blood vessel.

DETAILED DESCRIPTION

Figure 1:
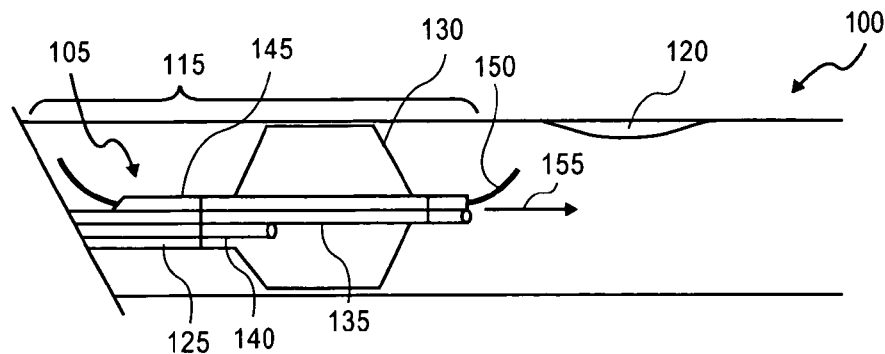
FIG. 1 shows a blood vessel and a first embodiment of a catheter assembly to deliver a treatment agent introduced into the blood vessel.
Figure 1:
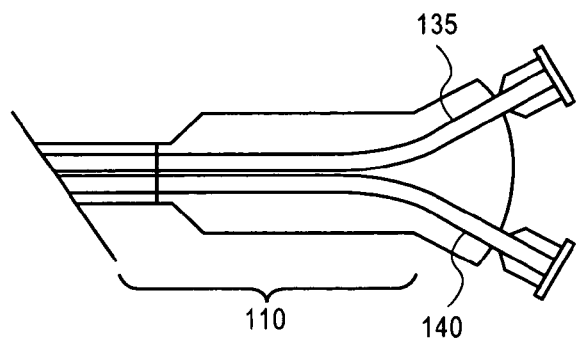

Pro-healing agent formulation compositions, methods and treatments for enhancing vascular healing are disclosed herein. In some embodiments, a pro-healing agent is delivered to a denuded or damaged endothelium treatment area in a blood vessel. In some embodiments, a pro-healing agent is encapsulated, suspended, disposed within or loaded into a biodegradable carrier for sustained-release delivery to a denuded or damaged endothelium treatment area in a blood vessel. In some applications, the pro-healing agent can accelerate re-endothelialization of a denuded vascular region. In some applications, the pro-healing agent can assist in the regaining of endothelium functionality. The formulation can be delivered by a delivery assembly such as a syringe, an infusion catheter, a porous balloon catheter, a needle injection catheter, a double balloon catheter or the like.

It is generally accepted that endothelial progenitor cells (EPC) are derived from bone marrow and circulate throughout the circulatory system. "Endothelial progenitor cells" are cells which are capable of giving rise to endothelium cells. Examples of generally accepted EPCs include, but are not limited to, CD34+/VEGFR2 and CD133/VEGFR2 positive cells. EPCs participate in maintaining the integrity and function of vascular endothelium and also in forming new blood vessels (angiogenesis).

Recent studies suggest that adhesion and transmigration are involved in the recruitment of EPCs to sites of tumor angiogenesis. Recruitment and incorporation of EPCs appears to require a coordinated sequence of multi-step adhesive and signaling events including chemoattraction, adhesion, and transmigration, and finally the differentiation to endothelial cells. Recent studies have shown that incorporation of endothelial progenitor cells in tissue without injury is low. However, in ischemic tissue, the incorporation of EPCs has been shown to vary from about 0% to about 90%.

The initial recruitment of EPCs to ischemic tissue involves adhesion of the endothelial progenitor cells to endothelial cells activated by cytokines and ischemia. In denuded arties, re-endothelialization is thought to occur by the adhesion of EPCs to extracellular matrix proteins. Adhesion of EPCs to denuded vessels appears to be mediated by vitronectin-receptors ($\alpha_v\beta_3$- and $\alpha_v\beta_5$-integrins). Transmigration of the endothelial progenitor cells through the endothelial cell monolayer follows.

Chemotaxis, migration and invasion appear to follow adhesion and transmigration. "Chemotaxis" is an innate behavioral response by an organism in which bodily cells or other single-cell or multicellular organisms direct their movements according to certain chemicals in their environment. Chemokines such as, for example, SDF-1, lipid mediators and factors released by heterologous cells, can serve as chemoattractants for EPCs, as can vasoendothelial growth factor (VEGF). The chemical environment therefore heavily influences the ability of the EPCs to migrate and invade the endothelial layer to eventually differentiate into endothelial cells.

Pro-Healing Agents

A pro-healing agent can include any agent that promotes re-endothelialization or assists in the regaining of endothelium functionality. As used herein, a "pro-healing agent" refers to an agent that induces a faster rate of re-endothelialization or helps damaged endothelium to recapture endothelial functionality (rehabilitation) relative to an untreated endothelium. In some embodiments, the pro-healing agent is a non-pharmaceutical treatment agent. Treatment agent and pro-healing agent are hereinafter used interchangeably.

A pro-healing agent can be generally categorized by the mechanism in which it promotes re-endothelialization or assists in the regaining of endothelium functionality. A mechanism can include a physical mechanism, a chemical mechanism or a combination thereof. A pro-healing agent that operates by a physical mechanism can provide, for example, docking sites for EPCs. A pro-healing agent that operates by a chemical mechanism can be, for example, a chemoattractant. An embodiment of the present invention contemplates indirect methods using a pro-healing agent for re-endothelialization and endothelial rehabilitation rather than direct methods. An example of a direct method can be, for example, delivery of EPCs to a treatment site. An example of an indirect method can be, for example, delivery of a pro-healing agent which physically binds to EPCs or chemically attracts EPCs to promote healing or rehabilitation at a treatment site.

In some embodiments, the pro-healing agent can be a growth factor. A "growth factor" is a protein that acts as a signaling molecule between cells and attaches to specific receptors on the surface of a target cell and promotes differentiation and maturation of these cells. Examples of growth factors include, but are not limited to, isoforms of vascular endothelial growth factor (VEGF), fibroblast growth factor (FGF, e.g. beta-FGF), Del 1, hypoxia inducing factor (HIF 1-alpha), monocyte chemoattractant protein (MCP-1), nicotine, platelet derived growth factor (PDGF), insulin-like growth factor 1 (IGF-1), transforming growth factor (TGF alpha), hepatocyte growth factor (HGF), estrogens, follistatin, proliferin, prostaglandin E1 and E2, tumor necrosis factor (TNF-alpha), interleukin 8 (Il-8), hematopoietic growth factors, erythropoietin, granulocyte-colony stimulating factors (G-CSF) and platelet-derived endothelial growth factor (PD-ECGF). Growth factors can serve as a chemoattractant thereby recruiting endogenous EPCs to a treatment site for re-endothelialization or endothelial rehabilitation. For example, it has been shown that VEGF produced by and released from the vessel wall can bind to VEGF receptors (flt-1, flk-1) on EPCs thereby stimulating the EPCs to adhere, migrate, and proliferate. Li B. et al., *VEGF and PlGF promote adult vasculogenesis by enhancing EPC recruitment and vessel formation at the site of tumor neovascularization*, FASEB J. 20: 1495-97, 2006.

In some embodiments, the pro-healing agent can be a natriuretic peptide. A "natriuretic peptide" is a polypeptide hormone involved in the homeostatic control of body water and sodium. Examples of natriuretic peptides include atrial natriuretic peptide (ANP), brain natriuretic peptide (BNP) and C-type natriuretic peptide (CNP). All nutriuretic peptides include a seventeen amino acid ring. The natriuretic factors bind to natriuretic receptors which in turn activate guanylate cyclase, protein kinase G, and specific transcription factors resulting in gene activation/inactivation that result in increased EPC adhesion, migration and proliferation.

In some embodiments, the pro-healing agent is an extracellular (EC) binding protein and/or peptide (hereinafter referred to interchangeably). EC binding peptides are peptides which include cell retention sites. Examples of EC binding peptides include, but are not limited to, arginine-glycine-aspartic acid peptide sequence (RGD), cyclic RGD, serine-isoleucine-lysine-valine-alanine-valine (SIKVAV, or IKVAV), tyrosine-isoleucine-glycine-serine-arginine (YIGSR) and the like. RGD is a common cell adhesion ligand and can increase the retention of endothelial cells to the treatment area. RGD is derived from fibronectin. YIGSR, SIKVAV and IKVAV are derived from laminin. EC binding peptides can provide docking sites for EPCs. Peptides such as RGD and YIGSR bind to specific integrins on the EPC cell surface. If these peptides are immobilized on a surface or substrate, this leads to the EPC adhering to the surface. Depending on the nature, and number of bound peptides, the EPC can be adhered but still able to migrate, or adhered so tightly it cannot migrate.

In some embodiments, the pro-healing agent is a glycoprotein. In some embodiments, osteopontin (OPN) is the pro-healing agent. OPN is a phosphorylated acidic glycoprotein containing RGD ligands and includes approximately 298 amino acids. OPN is known to be involved in regulatory functions including cell adhesion and migration. All of the above peptide binding motifs bind to specific integrin receptors (fibronectin receptor, laminin receptor) and form focal adhesions that recruit and activate focal adhesion kinase which then activates additional signaling molecules that ultimately change cell behavior, e.g., attachment, migration, proliferation. In some embodiments, laminin is the pro-healing agent. Laminins are a family of heterotrimeric glycoproteins found in the basal lamina underlying the epithelium. Laminins are known to be involved in biological activities including promotion of cell adhesion, migration, growth and differentiation. Laminins can provide reinforcement of the base layer on which the endothelium resides.

In some embodiments, the pro-healing agent is a hormone. For example, the pro-healing agent can be 17-β-estradiol (estradiol). Estradiol is an endogenous cholesterol derivative which helps to support bone growth. It is anticipated that estradiol may improve vascular healing, reduce smooth muscle cell migration and proliferation in damaged vessels. Estradiol binds to surface and nuclear estrogen receptors. The surface receptors activate nitric oxide synthase resulting in the production of nitric oxide; the resultant nitric oxide can then activate guanylate cyclase, and protein kinase G that alters gene expression. Alternatively, estradiol can bind to a nuclear receptor that then acts as a transcription factor that alters gene expression and changes cell behavior.

In some embodiments, the pro-healing agent is an antibody or fragment thereof. An antibody is a protein used by the immune system to identify and neutralize foreign objects such as bacteria and viruses. Immunoglobulins are glycoproteins that function as antibodies. Examples of antibodies include CD34 and CD133. Antibodies can provide docking sites for EPCs. Molecules such as CD34 and CD133 are cell surface glycoproteins. Antibodies to these glycoproteins will associate, or adhere, to the glycoproteins. The binding is not covalent, but consists of hydrogen bonding, polar interactions, and Vander Waals interactions. By attaching antibodies to CD34, for example, to a surface, EPCs will become attached to that surface.

In some embodiments, the pro-healing agent is an anti-inflammatory: A normal response to trauma in a vascular region is the attraction of immune cells. A large concentration of immune cells present for a prolonged period of time can create a state of chronic inflammation, and can cause destabilization of the endothelium. Examples of anti-inflammatories include, but are not limited to, steroidal and non-steroidal anti-inflammatory agents such as corticosteroids including clobetastol, dexamethasone and glucocorticoids. Anti-inflammatories can indirectly inhibit prostaglandins and leukotrienes, the two main products of inflammation.

In some embodiments, a pro-healing agent can be a super oxide dismutase and mimetics thereof, 4-amino-2,2,6,6-tetramethylpiperidine-1-oxyl (4-amino-TEMPO), a dietary supplement such as vitamin C and E, tacrolimus, P38 map kinase inhibitors including pyridinylimidazole compounds such as SB 203580, NFkb inhibitors including ubiquitin-proteosome pathway and proteasome inhibitors.

Carriers

In some embodiments, the pro-healing agent can be encapsulated, suspended, disposed within or loaded into a biodegradable carrier. Examples of biodegradable carriers include, but are not limited to, a liposome, a polymerosome, a micelle, a particle and a gel. Examples of particles include, but are not limited to, a microsphere, a nanosphere, a microrod and a nanorod. In some embodiments, the biodegradable carrier is formulated such that it is bioerodable when present in physiological conditions.

In some embodiments, a carrier can provide sustained release of a pro-healing agent. Sustained release may be beneficial when a controlled and deliberate delivery of the pro-healing agent is desirable. Because the environment in a blood vessel is subjected to constant pressure and movement of blood, a biodegradable sustained-release carrier with a pro-healing agent may provide a longer duration time in which the pro-healing agent is present as the carrier degrades over time and releases its load.

In some embodiments, the biodegradable carrier is a liposome. "Liposomes" are artificial vesicles that are approximately spherical in shape and can be produced from natural phospholipids and cholesterol. In one method, phospholipids are mixed with cholesterol in chloroform. Suitable phospholipids include, but are not limited to, dimyristoyl phosphatidyl choline or dipalmitoyl ethanolamine. In some embodiments, hydrophobic treatment agent can be added with an optional co-solvent, such as heptane or toluene. The liposomes may also be hydrophilically modified with an agent such as polyethylene glycol or dextran. After mixing, the solvent (and optional co-solvent) can be evaporated with heat or ambient temperature in a round bottom flask. Resultant lipids will be deposited on the glass surface. In some embodiments, hydrophilic treatment agent and water can be added to the flask and sonicated to form liposomes. The resultant suspension can be pressure filtered through ceramic pore size controlled filters to reduce liposome particle size. A liposome can be in a range in size from between about 25 nm to about 2000 nm.

In some embodiments, the biodegradable carrier is a polymerosome. "Polymerosomes" are polymer vesicles formed from di-block or tri-block copolymers with blocks of differing solubility. Polymerosomes may be formed by methods such as film rehydration, electro-formation and double emulsion. In some methods, a similar manufacturing technique can be used as that of a liposome to form polymerosomes. For example, in some embodiments, a polymerosome can be a di-block copolymer including a block which is hydrophobic, e.g., poly lactic acid, polycaprolactone, n-butyl acrylate, and another block which is hydrophilic, e.g., poly (ethylene glycol), poly(acrylic acid). A polymerosome can be in a range from between about 25 nm to about 2000 nm.

In some embodiments, the biodegradable carrier is a micelle. A "micelle" is an aggregate of surfactant or polymer molecules dispersed in a liquid colloid. Micelles are often globular in shape, but other shapes are possible, including ellipsoids, cylinders, bilayers, and vesicles. The shape of a micelle is controlled largely by the molecular geometry of its surfactant or polymer molecules, but micelle shape also depends on conditions such as temperature or pH, and the type and concentration of any added salt.

Micelles can be formed from individual block copolymer molecules, each of which contains a hydrophobic block and a hydrophilic block. The amphiphilic nature of the block copolymers enables them to self-assemble to form nanosized aggregates of various morphologies in aqueous solution such that the hydrophobic blocks form the core of the micelle, which is surrounded by the hydrophilic blocks, which form the outer shell The inner core of the micelle creates a hydrophobic microenvironment for a non-polar treatment agent, while the hydrophilic shell provides a stabilizing interface between the micelle core and an aqueous medium. Examples of polymers which can be used to form micelles include, but are not limited to, polycaprolactone polyethylene oxide blocks, polyethylene oxide-β-polypropylene oxide-β-polyethylene oxide triblock copolymer and copolymers which have a polypeptide or polylactic acid core-forming block and a polyethylene oxide block. A micelle can be in a range from between about 10 nm to about 100 nm.

In some embodiments, the sustained-release carrier is a nano or micro-particle. Various methods can be employed to formulate and infuse or load the particles with treatment agent. In some embodiments, the particles are prepared by a water/oil/water (W/O/W) double emulsion method. In the W1 phase, an aqueous phase containing treatment agent, is dispersed into the oil phase consisting of polymer dissolved in organic solvent (e.g., dichloromethane) using a high-speed homogenizer. Examples of sustained-release polymers include, but are not limited to, poly(D,L-lactide-co-glycolide) (PLGA), poly(D,L-lactide) (PLA) or PLA-PEG co-polymers, poly-ester-amide co-polymers (PEA) and poly-phosphazines. The primary water-in-oil (W/O) emulsion is then dispersed in an aqueous solution containing a polymeric surfactant, e.g., poly(vinyl alcohol) (PVA), and further homogenized to produce a W/O/W emulsion. After stirring for several hours, the particles are collected by filtration. A microparticle can be in a range from about 5 μm to about 200 μm, preferably 10 μm to 50 μm. A nanoparticle can be in a range from between about 10 nm to about 500 nm, preferably about 50 nm to about 300 nm.

In some embodiments, the sustained-release carrier is a nanofiber or nanorod (hereinafter referred to interchangeably) formed from self-assembled peptides. Nanorods can be formed by methods known by those skilled in the art, such as those described in J. D. Hartgerink, E. Beniash, and S. I. Stupp *Self-Assembly and Mineralization of Peptide Amphiphile Nanofibers*. Science, 294 (2001):1685-1688. J. D. Hartgerink, E. Beniash, S. I. Stupp *Peptide-Amphiphile Nanofibers: A versatile scaffold for the preparation of self-assembling materials*. PNAS, 99 (2002): 5133-5138.

In some embodiments, the sustained-release carrier is a gel. A "gel" is an apparently solid, jelly-like material formed from a colloidal solution. By weight, gels are mostly liquid, yet they behave like solids. In some embodiments, the gel is a solution of degradable polymers. For example, the gel can be PLA in benzyl benzoate. In some embodiments, the gel is a biodegradable, viscous gel. For example, the gel can be a solution of sucrose acetate isobutyrate. In the case where the gel consists of a water-miscible organic solvent plus a polymer, a process of phase inversion occurs when the gel is introduced into the body. As the solvent diffuses out, and the water diffuses in, the polymer phase inverts, or precipitates, forming a depot of varying porosity and morphology depending on the composition. Gels can also consist of water soluble polymers in an aqueous carrier. These can provide a faster release of drug or encapsulated agent.

In any of the above-described embodiments, a coating including a permeabilizing reagent can be applied to the carrier for enhanced uptake into the endothelium. In one embodiment, the permeabilizing reagent can be one of a calcium ion chelator, a surfactant, and a receptor-mediated permeabilizing reagent. More particularly, the permeabilizing reagent can be one of iminodiacetic acid, nitriloacetic acid, ethylenediaminomonoacetic acid, ethylenediaminodiacetic acid, ethylenediaminotetraacetic acid, sodium taurodihydrofusidate, sodium salicylate, sodium caprate, sodium glycocholate, cholylsarcosine, isopropyl myristate, partially hydrolyzed triglycerides, fatty-acid sugar derivatives, oleic acid derivatives, histamine, bradykinin and its conformational analogs, tumor necrosis factor alpha, nitroglycerine, sodium nitroprusside, diethylamine sodium, 3-morpholinosydnonimine, S-nitroso-N-acetyl-penicillamine, and vascular endothelial growth factor and combinations thereof. Commonly owned U.S. Pat. No. 7,014,861 describes permeabilizing reagents more specifically and is hereby incorporated by reference Delivery Devices Devices which can be used to deliver a free pro-healing treatment agent or a pro-healing agent encapsulated, suspended, disposed within or loaded into a biodegradable carrier, include, but are not limited to, a syringe, an infusion catheter, a porous balloon catheter, a double balloon catheter and the like.

FIG. 1 shows blood vessel 100 having catheter assembly 105 disposed therein. Catheter assembly 105 includes proximal portion 110 and distal portion 115. Proximal portion 110 may be external to blood vessel 100 and to the patient. Representatively, catheter assembly 105 may be inserted through a femoral artery and through, for example, a guide catheter and with the aid of a guidewire to a location in the vasculature of a patient. That location may be, for example, a coronary artery. FIG. 1 shows distal portion 115 of catheter assembly 105 positioned proximal or upstream from treatment site 120.

In one embodiment, catheter assembly 105 includes primary cannula 125 having a length that extends from proximal portion 110 (e.g., located external through a patient during a procedure) to connect with a proximal end or skirt of balloon 130. Primary cannula 125 has a lumen therethrough that, includes inflation cannula and delivery cannula 135. Each of inflation cannula 140 and delivery cannula 135 extends from proximal portion 110 of catheter assembly 105 to distal portion 115. Inflation cannula 140 has a distal end that terminates within balloon 130. Delivery cannula 135 extends through balloon 130.

Catheter assembly 105 also includes guidewire cannula 145 extending, in this embodiment, through balloon 130 through a distal end of catheter assembly 105. Guidewire cannula 145 has a lumen sized to accommodate guidewire 150. Catheter assembly 105 may be an over the wire (OTW) configuration where guidewire cannula 145 extends from a proximal end (external to a patient during a procedure) to a distal end of catheter assembly 105. Guidewire cannula 145 may also be used for delivery of a free pro-healing treatment agent or a pro-healing agent encapsulated, suspended, disposed within or loaded into a biodegradable carrier when guidewire 150 is removed with catheter assembly 105 in place. In such case, separate delivery cannula (delivery cannula 135) may be unnecessary or a delivery cannula may be used to delivery one treatment agent while guidewire cannula 145 is used to delivery another treatment agent.

In another embodiment, catheter assembly 800 is a rapid exchange (RX) type catheter assembly and only a portion of catheter assembly 800 (a distal portion including balloon 825) is advanced over guidewire 822. In an RX type of catheter assembly, typically, the guidewire cannula/lumen extends from the distal end of the catheter to a proximal guidewire port spaced distally from the proximal end of the catheter assembly. The proximal guidewire port is typically spaced a substantial distance from the proximal end of the catheter assembly. FIG. 1 shows an RX type catheter assembly.

In one embodiment, catheter assembly 105 is introduced into blood vessel 100 and balloon 130 is inflated (e.g., with a suitable liquid through inflation cannula 140) to occlude the blood vessel. Following occlusion, a solution (fluid) including a free pro-healing treatment agent or a pro-healing agent encapsulated, suspended, disposed within or loaded into a biodegradable carrier is introduced through delivery cannula 135 (arrow 155). A suitable solution of a free pro-healing treatment agent or a pro-healing agent encapsulated, suspended, disposed within or loaded into a biodegradable carrier is about 10 to about 2000 µL in preferably an isotonic solution at physiologic pH (i.e. phosphate buffered saline. By introducing a pro-healing agent in this manner, re-endothelialization and/or rehabilitation of the endothelium may occur.

Figure 2:
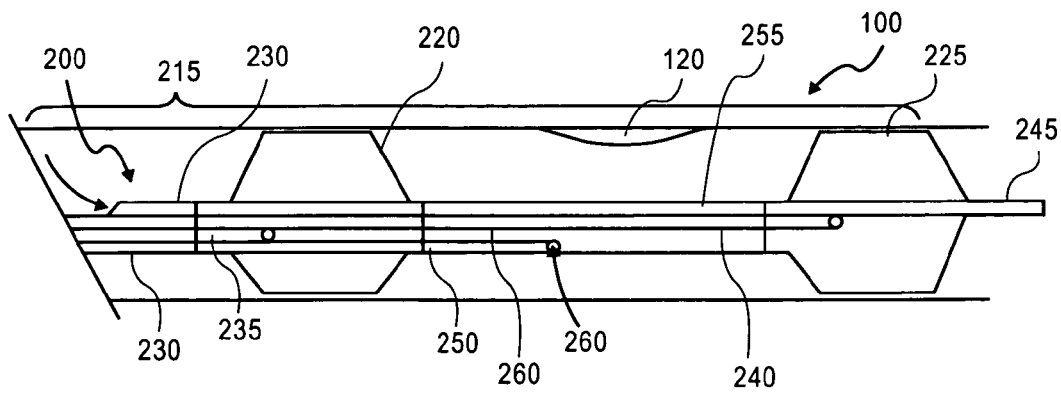
FIG. 2 shows a blood vessel and a second embodiment of a catheter assembly to deliver a treatment agent introduced into the blood vessel.
Figure 2:
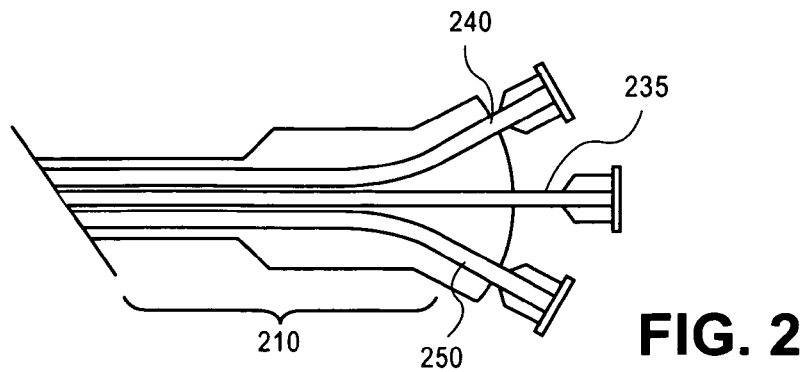

In an effort to improve the target area of a free pro-healing treatment agent or a pro-healing agent encapsulated, suspended, disposed within or loaded into a biodegradable carrier to a treatment site, such as treatment site 120, the injury site may be isolated prior to delivery. FIG. 2 shows an embodiment of a catheter assembly having two balloons where one balloon is located proximal to treatment site 120 and a second balloon is located distal to treatment site 120. Catheter assembly 200 includes proximal portion 210 and distal portion 215. FIG. 2 shows catheter assembly 200 disposed within blood vessel 100. Catheter assembly 200 has a tandem balloon configuration including proximal balloon 220 and distal balloon 225 aligned in series at a distal portion of the catheter assembly. Catheter assembly 200 also includes primary cannula 230 having a length that extends from a proximal end of catheter assembly 200 (e.g., located external to a patient during a procedure) to connect with a proximal end or skirt of balloon 220. Primary cannula 230 has a lumen therethrough that includes inflation cannula 235 and inflation cannula 240. Inflation cannula 235 extends from a proximal end of catheter assembly 200 to a point within balloon 220. Inflation cannula 235 has a lumen therethrough allowing balloon 220 to be inflated through inflation cannula 235. In this embodiment, balloon 220 is inflated through an inflation lumen separate from the inflation lumen that inflates balloon 225. Inflation cannula 240 has a lumen therethrough allowing fluid to be introduced in the balloon 225 to inflate the balloon. In this manner, balloon 220 and balloon 225 may be separately inflated. Each of inflation cannula 235 and inflation cannula 240 extends from, in one embodiment, the proximal end of catheter assembly 200 through a point within balloon 220 and balloon 225, respectively.

Catheter assembly 200 also includes guidewire cannula 245 extending, in this embodiment, through each of balloon 220 and balloon 225 through a distal end of catheter assembly. Guidewire cannula 245 has a lumen therethrough sized to accommodate a guidewire. In this embodiment, no guidewire is shown within guidewire cannula 245. Catheter assembly 200 may be an over the wire (OTW) configuration or a rapid exchange (RX) type catheter assembly. FIG. 2 illustrates an RX type catheter assembly.

Catheter assembly 200 also includes delivery cannula 250. In this embodiment, delivery cannula extends from a proximal end of catheter assembly 200 through a location between balloon 220 and balloon 225. Secondary cannula 255 extends between balloon 220 and balloon 225. A proximal portion or skirt of balloon 220 connects to a distal end of secondary cannula 255. A distal end or skirt of balloon 220 is connected to a proximal end of secondary cannula 255. Delivery cannula 250 terminates at opening 260 through secondary cannula 255. In this manner, a free pro-healing treatment agent or a pro-healing agent encapsulated, suspended, disposed within or loaded into a biodegradable carrier may be introduced between balloon 220 and balloon 225 positioned between treatment site 210.

FIG. 2 shows balloon 220 and balloon 225 each inflated to occlude a lumen of blood vessel 100 and isolate treatment site 120. In one embodiment, each of balloon 220 and balloon 225 are inflated to a point sufficient to occlude blood vessel 100 prior to the introduction of a free pro-healing treatment agent or a pro-healing agent encapsulated, suspended, disposed within or loaded into a biodegradable carrier. A free pro-healing treatment agent or a pro-healing agent encapsulated, suspended, disposed within or loaded into a biodegradable carrier is then introduced.

In the above embodiment, separate balloons having separate inflation lumens are described. It is appreciated, however, that a single inflation lumen may be used to inflate each of balloon 220 and balloon 225. Alternatively, in another embodiment, balloon 225 may be a guidewire balloon configuration such as a PERCUSURG™ catheter assembly where catheter assembly 200 including only balloon 220 is inserted over a guidewire including balloon 225.

Figure 3:
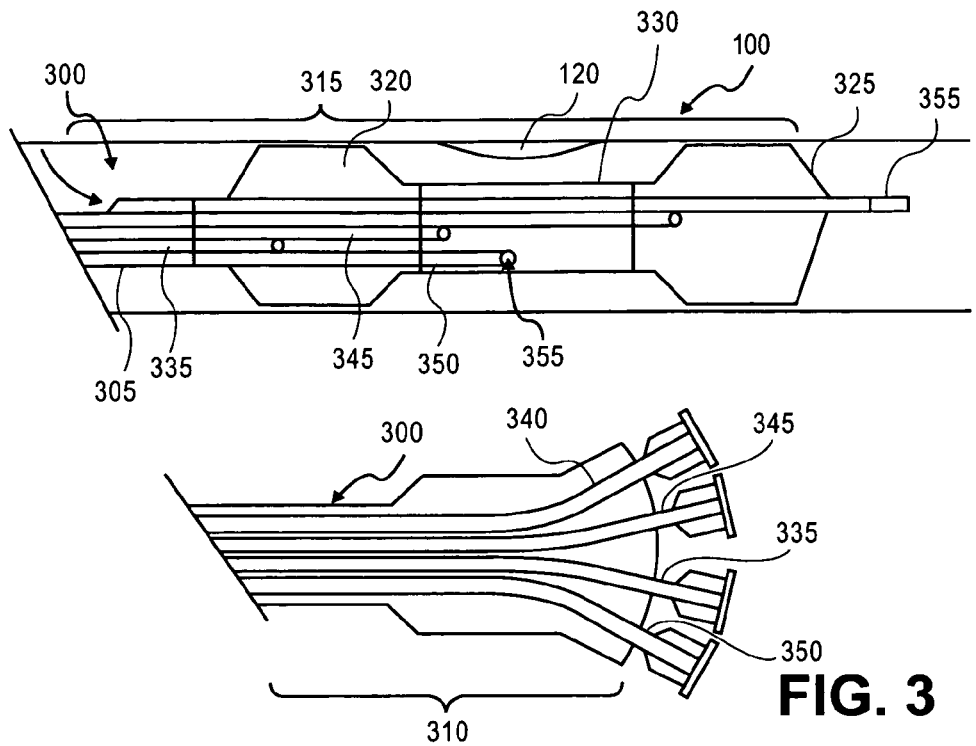
FIG. 3 shows a blood vessel and a third embodiment of a catheter assembly to deliver a treatment agent introduced into the blood vessel.

FIG. 3 shows catheter assembly 300 disposed within a lumen of blood vessel 100. Catheter assembly 300 includes proximal portion 310 and distal portion 315. Catheter assembly 300 has a tandem balloon configuration similar to the configuration described with respect to catheter assembly 200 of FIG. 2. In this case, the portion between the tandem balloons is also inflatable. FIG. 3 shows catheter assembly 300 including primary cannula or tubular member 305. In one embodiment, primary cannula 305 extends from a proximal end of the catheter assembly (proximal portion 310) intended to be external to a patient during a procedure, to a point proximal to a region of interest or treatment site within a patient, in this case, proximal to treatment site 120. Representatively, catheter assembly 300 may be percutaneously inserted via femoral artery or a radial artery and advanced into a coronary artery.

Primary cannula 305 is connected in one embodiment to a proximal end (proximal skirt) of balloon 320. A distal end (distal skirt) of balloon 320 is connected to secondary cannula 330. Secondary cannula 330 has a length dimension, in one embodiment, suitable to extend from a distal end of a balloon located proximal to a treatment site beyond a treatment site. In this embodiment, secondary cannula 330 has a property such that it may be inflated to a greater than outside diameter than its outside diameter when it is introduced (in other words, secondary cannula 330 is made of an expandable material). A distal end of secondary cannula 330 is connected to a proximal end (proximal skirt of balloon 325). In one embodiment, each of balloon 320, balloon 325, and secondary cannula 330 are inflatable. Thus, in one embodiment, each of balloon 320, balloon 325, and secondary cannula 330 are inflated with a separate inflation cannula. FIG. 3 shows catheter assembly having inflation cannula 335 extending from a proximal end of catheter assembly 300 to a point within balloon 320; inflation cannula 340 extending from a proximal end of catheter assembly 300 to a point within balloon 325; and inflation cannula 345 extending from a proximal end of catheter assembly 300 to a point within secondary cannula 330. In another embodiment, the catheter assembly may have a balloon configured in a dog-bone arrangement such that inflation of the balloon through a single inflation lumen inflates each of what are described in the figures as separated balloon 320, balloon 325 and secondary cannula 330. Catheter assembly 300 also includes guidewire cannula (no guidewire shown in this embodiment).

By using an expandable structure such as secondary cannula 330 adjacent a treatment site, the expandable structure may be expanded to a point such that a pro-healing agent encapsulated, suspended, disposed within or loaded into a biodegradable carrier may be dispensed very near or at the treatment site. FIG. 3 shows catheter assembly 300 including delivery cannula 350 extending from a proximal end of catheter assembly 300 through primary cannula 305, through balloon 320 and into secondary cannula 325. Delivery cannula 350 terminates at dispensing port 355 within secondary cannula 330. As viewed, secondary cannula 330 is expandable to an outside diameter less than an expanded outside diameter of balloon 320 or balloon 325 (e.g., secondary cannula 330 has an inflated diameter less than an inner diameter of blood vessel 100 at a treatment site).

Figure 4:
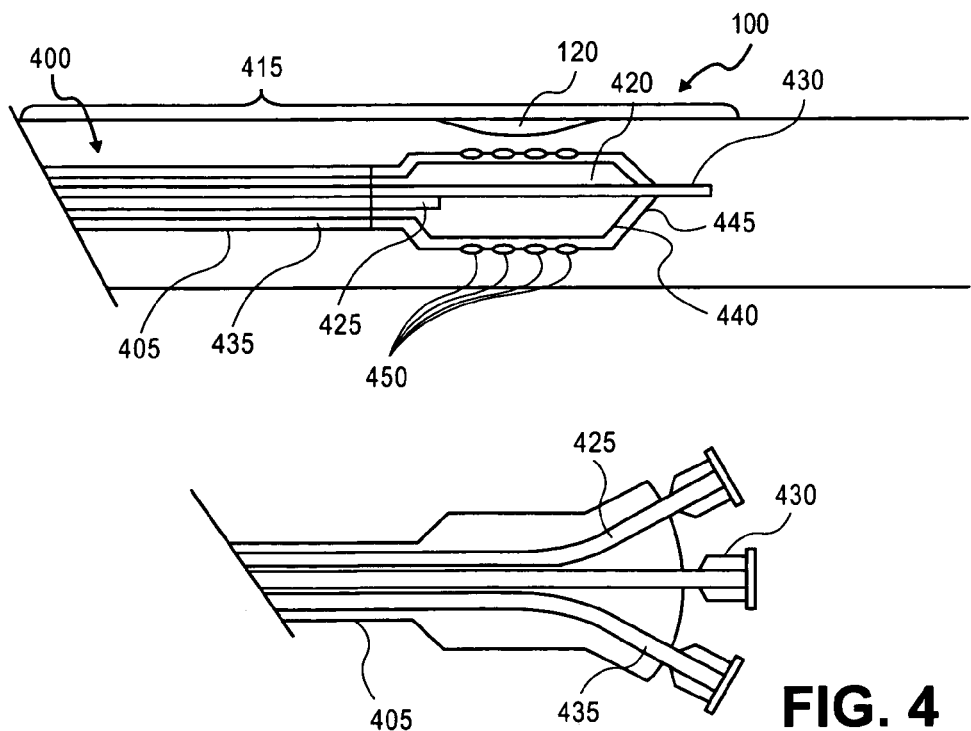
FIG. 4 shows a blood vessel and a fourth embodiment of a catheter assembly to deliver a treatment agent introduced into the blood vessel.

FIG. 4 shows another embodiment of a catheter assembly. Catheter assembly 400, in this embodiment, includes a porous balloon through which a treatment agent, such as a pro-healing agent encapsulated, suspended, disposed within or loaded into a biodegradable carrier, may be introduced. FIG. 4 shows catheter assembly 300 disposed within blood vessel 100. Catheter assembly 400 includes proximal portion 410 and distal portion 415. Catheter assembly 400 has a porous balloon configuration positioned at treatment site 120. Catheter assembly 400 includes primary cannula 405 having a length that extends from a proximal end of catheter assembly 400 (e.g., located external to a patient during a procedure) to connect with a proximal end or skirt of balloon 420. Primary cannula 405 has a lumen therethrough that includes inflation cannula 425. Inflation cannula 425 extends from a proximal end of catheter assembly 400 to a point within balloon 420. Inflation cannula 425 has a lumen therethrough allowing balloon 420 to be inflated through inflation cannula 425.

Catheter assembly 400 also includes guidewire cannula 430 extending, in this embodiment, through balloon 420. Guidewire cannula 430 has a lumen therethrough sized to accommodate a guidewire. In this embodiment, no guidewire is shown within guidewire cannula 430. Catheter assembly 400 may be an over-the-wire (OTW) configuration or rapid exchange (RX) type catheter assembly. FIG. 4 illustrates an OTW type catheter assembly.

Catheter assembly 400 also includes delivery cannula 435. In this embodiment, delivery cannula 435 extends from a proximal end of catheter assembly 400 to proximal end or skirt of balloon 420. Balloon 420 is a double layer balloon. Balloon 420 includes inner layer 440 that is a non-porous material, such as PEBAX, Nylon or PET. Balloon 420 also includes outer layer 445. Outer layer 445 is a porous material, such as extended polytetrafluoroethylene (ePTFE). In one embodiment, delivery cannula 435 is in fluid communication with the space between inner layer 440 and outer layer 445 so that a free pro-healing agent or a pro-healing agent encapsulated, suspended, disposed within or loaded into a biodegradable carrier can be introduced between the layers and permeate through pores 450 on outer layer 445 into a lumen of blood vessel 100.

As illustrated in FIG. 4, in one embodiment, catheter assembly is inserted into blood vessel 100 so that balloon 420 is aligned with treatment site 120. Following alignment of balloon 420 of catheter assembly 400, balloon 420 may be inflated by introducing an inflation medium (e.g., liquid through inflation cannula 425). In one embodiment, balloon 420 is only partially inflated or has an inflated diameter less than an inner diameter of blood vessel 100 at treatment site 120. In this manner, balloon 420 does not contact or only minimally contacts the blood vessel wall. A suitable expanded diameter of balloon 420 is on the order of 2.0 to 5.0 mm for coronary vessels. It is appreciated that the expanded diameter may be different for peripheral vasculature. Following the expansion of balloon 420, a treatment agent, such as a free pro-healing agent or a pro-healing agent encapsulated, suspended, disposed within or loaded into a biodegradable carrier, is introduced into delivery cannula 435. The treatment agent can flow through delivery cannula 435 into a volume between inner layer 440 and outer layer 445 of balloon 420. At a relatively low pressure (e.g., on the order of two to four atmospheres (atm)), the treatment agent then permeates through the pores 450 of outer layer 445 into blood vessel 100.

Figure 5:
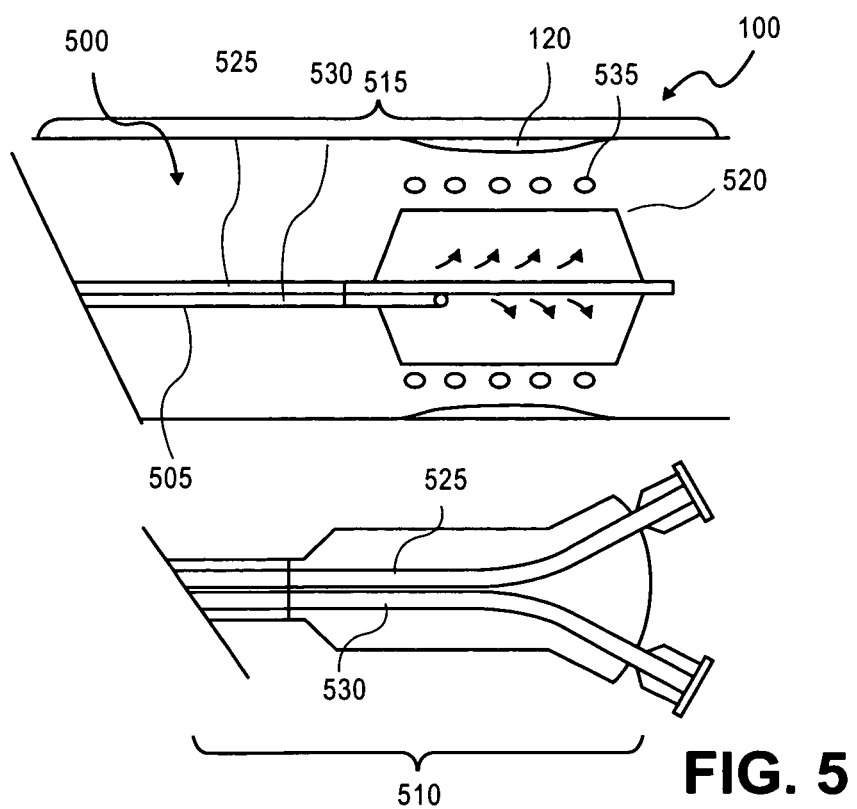
FIG. 5 shows a blood vessel and a fifth embodiment of a catheter assembly to deliver a treatment agent introduced into the blood vessel.

FIG. 5 shows another embodiment of a catheter assembly suitable for introducing a treatment agent into a blood vessel. FIG. 5 shows catheter assembly 500 disposed within blood vessel 100. Catheter assembly 500 includes proximal portion 510 and distal portion 515. Catheter assembly 500 includes primary cannula 505 having a length that extends from a proximal end of catheter assembly 500 (e.g., located external to a patient during a procedure) to connect with a proximal and/or skirt of balloon 520. Balloon 520, in this embodiment, is located at a position aligned with treatment site 120 in blood vessel 100.

Disposed within primary cannula 505 is guidewire cannula 525 and inflation cannula 530. Guidewire cannula 525 extends from a proximal end of catheter assembly 500 through balloon 520. A distal end or skirt of balloon 520 is connected to a distal portion of guidewire cannula 525.

Inflation cannula 530 extends from a proximal end of catheter assembly 500 to a point within balloon 520. In one embodiment, balloon 520 is made of a porous material such as ePTFE. A suitable pore size for an ePTFE balloon material is on the order of one micron (µm) to 60 µms. The porosity of ePTFE material can be controlled to accommodate a treatment agent flow rate or particle size by changing a microstructure of an ePTFE tape used to form a balloon, for example, by wrapping around a mandrel. Alternatively, pore size may be controlled by controlling the compaction process of the balloon, or by creating pores (e.g., micropores) using a laser.

ePTFE as a balloon material is a relatively soft material and tends to be more flexible and conformable with tortuous coronary vessels than conventional balloons. ePTFE also does not need to be folded which will lower its profile and allow for smooth deliverability to distal lesions and the ability to provide therapy to targeted or regional sites post angioplasty and/or stent deployment.

A size of balloon 520 can also vary. A suitable balloon diameter is, for example, in the range of two to five millimeters (mm). A balloon length may be on the order of eight to 60 mm. A suitable balloon profile range is, for example, approximately 0.030 inches to 0.040 inches.

Figure 6:
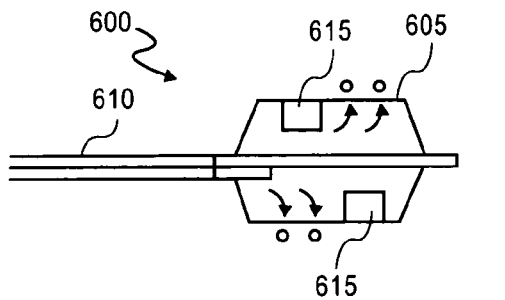
FIGS. 6-10 show various modified embodiments of the catheter assembly in FIG. 5 to deliver a treatment agent introduced into the blood vessel.

In one embodiment, a porous balloon may be masked in certain areas along its working length to enable more targeted delivery of a treatment agent. FIG. 6 shows an embodiment of porous balloon masked in certain areas. Catheter assembly 600 includes balloon 605 connected to primary cannula 610. Balloon 605 is a porous material such as ePTFE with masks 615 of a nonporous material (e.g., Nylon) positioned along a working length of balloon 605.

Figure 7:
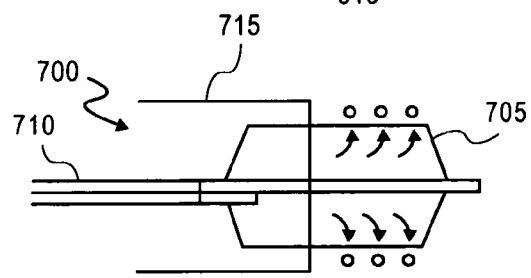

In another embodiment, a sheath may be advanced over a porous balloon (or the balloon withdrawn into a sheath) to allow tailoring of a treatment agent distribution. FIG. 7 shows catheter assembly 700 including balloon 705 connected to primary cannula 710. Sheath 715 is located over a portion of balloon 705 (a proximal portion of the working length).

Figure 8:
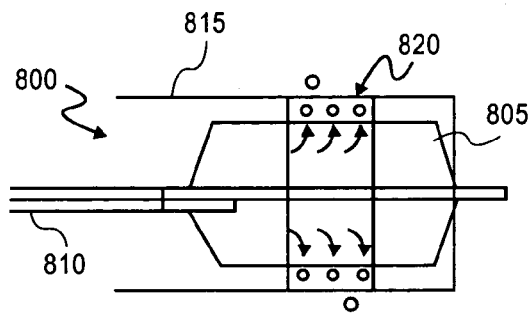

In another embodiment, a sheath may have a window for targeting delivery of the treatment agent through a porous balloon. FIG. 8 shows catheter assembly 800 including balloon 805 connected to primary cannula 810. Sheath 815 is extended over a working length of balloon 805. Sheath 815 has window 820 that provides an opening between the sheath and balloon 805.

Figure 9:
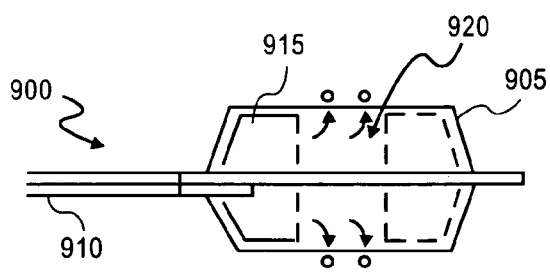

In another embodiment, a liner inside a porous balloon may be used to target preferential treatment agent delivery. For example, the liner may have a window through which a treatment agent is delivered, e.g., on one side of a liner for delivery to one side of a vessel wall. This type of configuration may be used to address eccentric lesions. FIG. 9 shows catheter assembly 900 including balloon 905 of a porous material connected to primary cannula 910. Disposed within (e.g., connected to an inner wall of) balloon 905 is liner 915 of a non-porous material such as Nylon. FIG. 9 also shows opening or window 920 between liner portions that allow a material to exit pores in balloon 905. Alternatively, a liner may have a tailored distribution of pores along the liner. The orientation of the balloon liner may be visualized through radio-opaque markers or through indicators on the external portion of catheter assembly 900.

Figure 10:
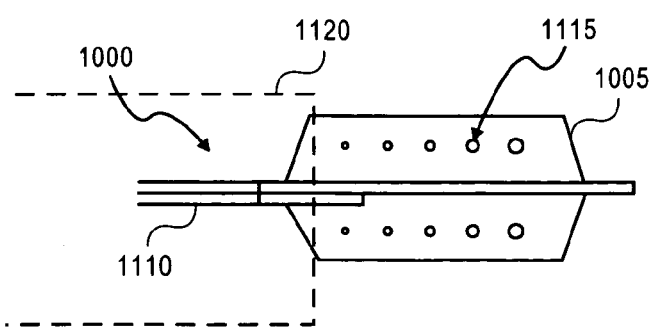

In an alternative embodiment, rather than using a porous material like ePTFE for forming a porous balloon, a conventional balloon material such as PEBAX, Nylon or PET may be used that has tens or hundreds of micropores around its circumference for treatment agent diffusion. A suitable pore size may range, for example, from approximately five to 100 microns. Pores may be created by mechanical means or by laser perforation. Pore distribution along a balloon surface may be non-homogeneous to tailor distribution of treatment agent delivery. For example, FIG. 10 shows catheter assembly 1000 including balloon 1005 connected to primary cannula 1110. Balloon 1005 has a number of openings or pores 1115 extending in a lengthwise direction along the working length of balloon 1005. The pores get gradually larger along its length (proximal to distal). FIG. 10 shows two rows of pores 1115 as an example of a pore distribution. In other examples, pores 1115 may be created only on one side of balloon 1115 to deliver a treatment agent preferentially to one side of a blood vessel (e.g., to address eccentric lesions). The orientation of balloon 1005 in this situation may be visualized through radio-opaque markers, or through indicators on an external portion of catheter assembly 1000. Balloon 1005 may also be retractable into optional sheath 1120 to tailor a length of treatment agent delivery. In an alternative embodiment, sheath 1120 may have an opening on one side to preferentially deliver a treatment agent to one side of the vessel.

According to any of the embodiments described with reference to FIGS. 5-17 and the accompanying text, a treatment agent such as a free pro-healing agent or a pro-healing agent encapsulated, suspended, disposed within or loaded into a biodegradable carrier, may be introduced through the inflation cannula (e.g., inflation cannula 530) to expand the balloon (e.g., balloon 520). In the example of a balloon of a porous material, such as balloon 520, the treatment agent will expand balloon 520 and at relatively low pressure (e.g., 2-4 atm) diffuse through pores in the porous balloon material to treatment site 120 within a lumen of blood vessel 100. FIG. 5 shows treatment agent 535 diffusing through balloon 520 into a lumen of blood vessel 100. Since balloon 520 is positioned at treatment site 120, treatment agent 535 is diffused at or adjacent (e.g., proximal or distal) to treatment site 120.

FIG. 11 shows another embodiment of a catheter assembly suitable for introducing a treatment agent at a treatment site. FIG. 11 shows catheter assembly 1100 disposed within blood vessel 100. Catheter assembly 1100 includes proximal portion 1110 and distal portion 1115. In this embodiment, catheter assembly 1100 utilizes an absorbent possibly porous device such as a sponge or a brush, connected to a catheter to dispense a treatment agent.

In one embodiment, catheter assembly 1100 includes guidewire cannula 1120 extending from a proximal end of catheter assembly 1120 (e.g., external to a patient during a procedure) to a point in blood vessel 100 beyond treatment site 120. Overlying guidewire cannula 1120 is primary cannula 1125. In one embodiment, primary cannula 1125 has a lumen therethrough of a diameter sufficient to accommodate guidewire cannula 1120 and to allow a treatment agent to be introduced through primary cannula 1125 from a proximal end to a treatment site. In one embodiment, catheter assembly 1100 includes a brush or sponge material 1130 connected at a distal portion of primary cannula 1125. Sponge 1130 has an exterior diameter that, when connected to an exterior surface of primary cannula 1125 will fit within a lumen of blood vessel 100. Catheter assembly 1100 also includes retractable sheath 1135 overlying primary cannula 1125. During insertion of catheter assembly 1100 into a blood vessel to a treatment site, sponge 1130 may be disposed within sheath 1135. Once catheter assembly 1100 is disposed at a treatment site, sheath 1135 may be retracted to expose sponge 1130. FIG. 11 shows sheath 1135 retracted, such as by pulling the sheet in a proximal direction.

In one embodiment, prior to insertion of catheter assembly 1100, sponge 1130 may be loaded with a treatment agent. Representatively, sponge 1130 may be loaded with a free pro-healing agent or a pro-healing agent encapsulated, suspended, disposed within or loaded into a biodegradable carrier.

In one embodiment, catheter assembly 1100 may provide for additional introduction of a treatment agent through primary cannula 1125. FIG. 11 shows primary cannula 1125 having a number of dispensing ports 1140 disposed in series along a distal portion of primary cannula 1125 coinciding with a location of sponge 1130. In this manner, once sponge 1130 is placed at treatment site 120 within blood vessel 100, additional treatment agent may be introduced through primary cannula 1125 if desired.

FIG. 12 shows another embodiment of a catheter assembly suitable for introducing a treatment agent into a blood vessel. FIG. 12 shows catheter assembly 1200 disposed within blood vessel 100. Catheter assembly 1200 includes proximal portion 1210 and distal portion 1215. Catheter assembly 1200 includes primary cannula 1220 having a length that extends from a proximal end of catheter assembly 1200 (e.g., located external to a patient during a procedure) to connect with a proximal end or skirt of balloon 1225. Balloon 1225, in this embodiment, is located at a position aligned with treatment site 120 in blood vessel 100.

In one embodiment, catheter assembly 1200 has a configuration similar to a dilation catheter, including guidewire cannula 1230 and inflation cannula 1235 disposed within primary cannula 1220. Guidewire cannula 1230 extends through balloon 1225 and balloon 1225 is connected to a distal end or skirt of guidewire cannula 1230. Inflation cannula 1235 extends to a point within balloon 1225.

In one embodiment, catheter assembly 1200 includes sleeve 1240 around a medial working length of balloon 1225. Balloon 1225, including a medial working length of balloon 1225, may be made of a non-porous material (e.g., a non-porous polymer). In one embodiment, sleeve 1240 is a porous material that may contain a treatment agent such as a free pro-healing agent or a pro-healing agent encapsulated, suspended, disposed within or loaded into a biodegradable carrier as described above. A representative material for sleeve 1240 is a silastic material. Sleeve 1240 may be loaded with or soaked (e.g., saturated) in a treatment agent before inserting catheter assembly 1200 into a blood vessel. Representatively, the pores of the porous sleeve may be filled with agent beforehand. The pores can also expand upon balloon inflation to deliver a treatment agent.

Figure 13:
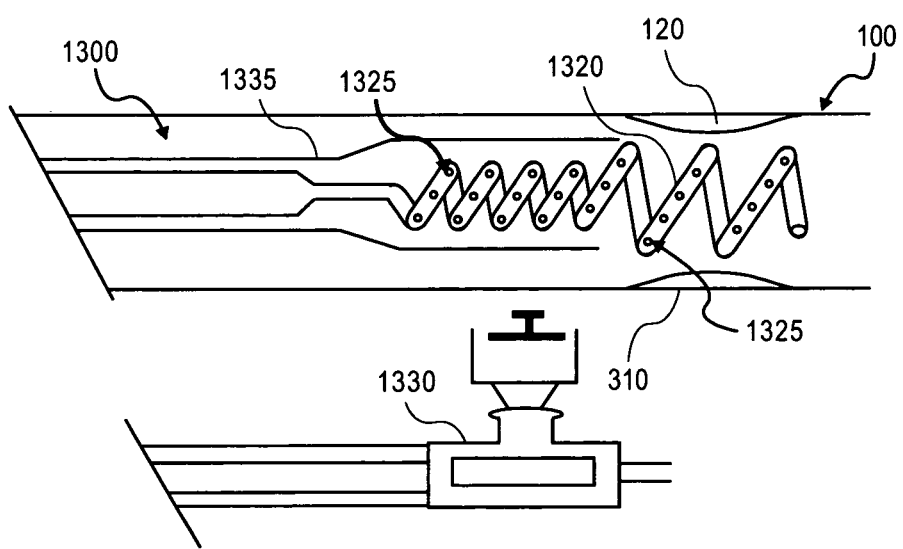
FIG. 13 shows a blood vessel and an eighth embodiment of a catheter assembly to deliver a treatment agent introduced into the blood vessel.

FIG. 13 shows another embodiment of a catheter assembly suitable for dispensing a treatment agent into a blood vessel. The catheter assembly of FIG. 13 relies on a flexible polymeric or metal hollow coil with microporous perfusion holes to deliver a treatment agent into a blood vessel. FIG. 13 shows catheter assembly 1300 including coil 1320 disposed from a proximal end of the catheter assembly (e.g., intended to be external to a patient during a procedure) to a point within a blood vessel, such as treatment site 120 of blood vessel 100. In one embodiment, coil 1320 is formed from a material that has a hollow cross-section, such as a hypo-tube or extrusion. In the embodiment shown, only a distal portion of coil 1320 is coiled, with the remaining portion being linear. A representative length of a distal portion of coil 1320 is on the order of one to 15 centimeters (cm). In addition, coil may be tapered from proximal to distal having (e.g., a reduced diameter at a distal end) to accommodate narrowing of blood vessels towards distal portion. Alternatively, coil may be in linear configuration in sheath (during delivery before deployment and during catheter retraction after deployment). This may be achieved by using a shape memory material such as Nitinol.

At a distal portion of coil 1320 (e.g., the coiled portion), a number (e.g., hundreds) of perfusion holes or micropores 1325 are formed to release a treatment agent therethrough. A suitable hole or micropore diameter is on the order of five to 100 microns formed, for example, around a circumference of a distal portion of coil 1320 using a laser. A proximal end of coil 1320 is connected to delivery hub 1330. A treatment agent, such as a free pro-healing treatment agent or a pro-healing agent encapsulated, suspended, disposed within or loaded into a biodegradable carrier, can be injected through delivery hub 1330 and exit through holes or micropores 1325.

Catheter assembly 1300 includes sheath 1335. Sheath 1335 may be used to deliver coil 1320 to a treatment site and then retracted to expose at least a portion of the distal portion of coil 1320 including holes or micropores 1325. For delivery to a treatment site, a distal end of coil 1320 is tightly wound in either a clockwise or counterclockwise configuration. For delivery of a treatment agent, a distal portion of coil 1320 may be unwound, either by inflation through pressurization or through re-expansion into a previously memorized shape (e.g., where coil is a shape-memory material such as a nickel-titanium alloy). After a treatment agent has been introduced through pores 1325, a distal portion of coil 1320 may be withdrawn, either by deflation or by withdrawal into sheath 1335.

To minimize potential trauma to a vessel wall by shearing of the coil and against the vessel wall, a distal end of coil 1320 may be rounded or have a small sphere. Alternatively, two coils of opposite helicity may be joined at their distal end but not at overlaps in between. In another embodiment, the delivery system may consist of joined "Vs" which are rolled into a cylindrical configuration around an axis orthogonal to a plane of the Vs. Tightly wound in this configuration, a catheter assembly may be delivered to a treatment site where it is unwound to deliver a treatment agent through pores incorporated into the system.

In any of the embodiments of utilizing a coil to deliver a treatment agent, a pore distribution along a distal portion of the coil may be non-uniform to deliver the treatment agent preferentially to specific sites within a treatment area (e.g., to one side of a blood vessel).

A flexibility and profile of coil 1320 allows for regional treatment agent delivery in one embodiment up to approximately 15 centimeters long in a coronary vessel. An outer diameter of a hollow coil can range from 0.005 inches to 0.010 inches, and a wall thickness may range from 0.0005 inches to 0.003 inches. Treatment agent distribution may be controlled by pitch length of coil 1320.

Figure 14:
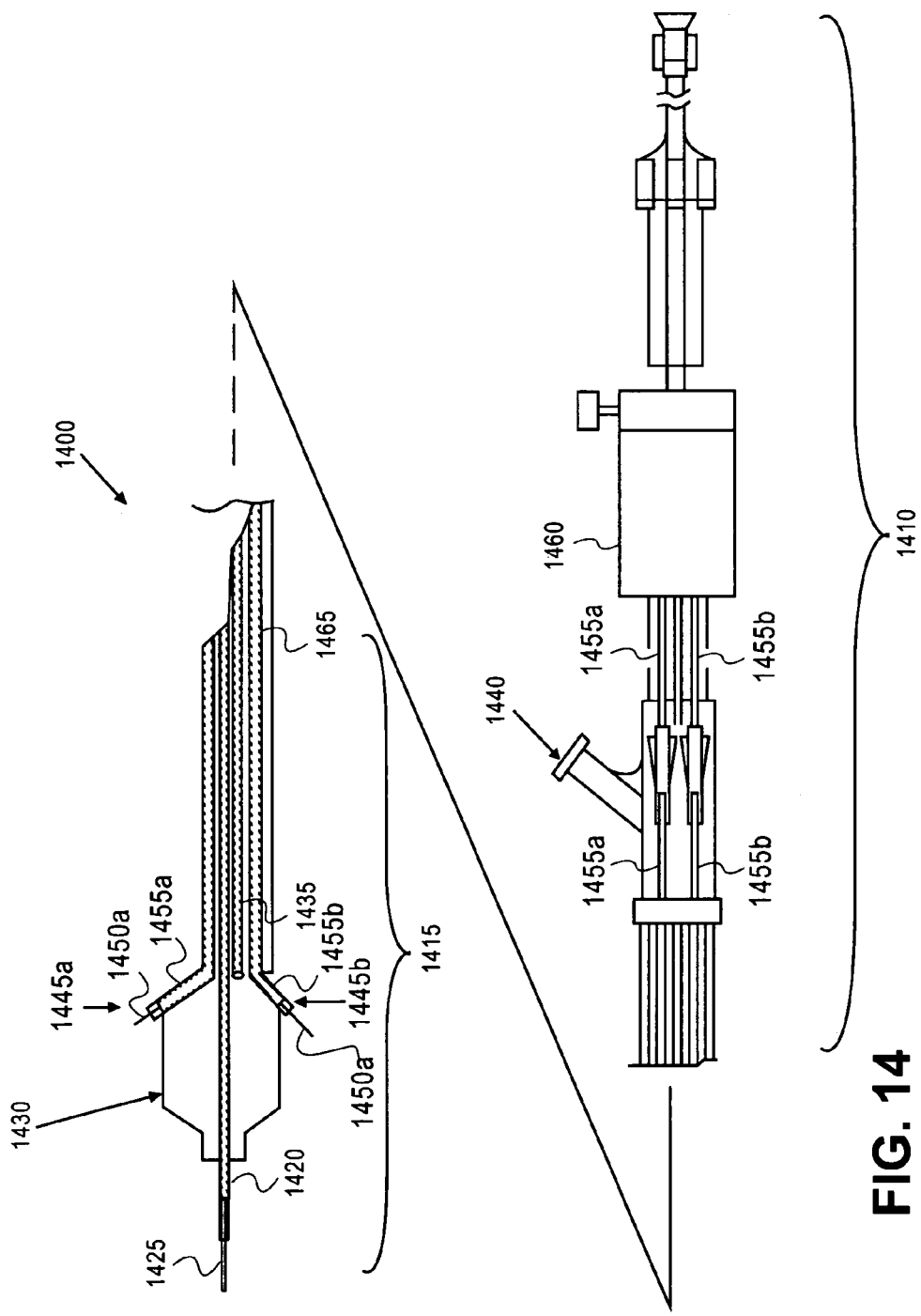
FIG. 14 shows an embodiment of a dual-needle catheter assembly to deliver a treatment agent introduced into the blood vessel.

FIG. 14 illustrates a dual needle injection device which can be used pursuant to the present invention. In general, the catheter assembly 1400 provides a system for delivering a treatment agent, such as a free pro-healing treatment agent or a pro-healing agent encapsulated, suspended, disposed within or loaded into a biodegradable carrier, to or through a desired area of a blood vessel (a physiological lumen) or tissue in order to treat a localized area of the blood vessel or to treat a localized area of tissue possibly located adjacent to the blood vessel. The catheter assembly 1400 is similar to the catheter assembly described in commonly-owned, U.S. Pat. No. 6,554,801, titled "Directional Needle Injection Drug Delivery Device", and incorporated herein by reference.

In one embodiment, catheter assembly 1400 is defined by elongated catheter body 1465 having proximal portion 1415 and distal portion 1410. Guidewire cannula 1420 is formed within catheter body (from proximal portion 1410 to distal portion 1415) for allowing catheter assembly 1400 to be fed and maneuvered over guidewire 1425. Balloon 1430 is incorporated at distal portion 1415 of catheter assembly 1400 and is in fluid communication with inflation cannula 1435 of catheter assembly 1400.

Balloon 1430 can be selectively inflatable to dilate from a collapsed configuration to a desired and controlled expanded configuration. Balloon 1430 can be selectively dilated (inflated) by supplying a fluid into inflation cannula 1435 at a predetermined rate of pressure through inflation port 1440. Balloon 1430 is selectively deflatable to return to the collapsed configuration or a deflated profile after inflation. Balloon 1430 may be dilated (inflated) by the introduction of a liquid into inflation cannula 1435. Liquids containing treatment and/or diagnostic agents may also be used to inflate balloon 1430. In one embodiment, balloon 1430 may be made of a material that is permeable to such treatment and/or diagnostic liquids. To inflate balloon 1430, the fluid can be supplied into inflation cannula 1435 at a predetermined pressure, for example, between about one and 20 atmospheres. The specific pressure depends on various factors, such as the thickness of balloon wall, the material from which balloon wall is made, the type of substance employed and the flow-rate that is desired.

Catheter assembly 1400 also includes substance delivery assemblies 1445a and 1445b for injecting a substance into a tissue of a physiological passageway. In one embodiment, substance delivery assemblies 1445a and 1445b include needles 1450a and 1450b, respectively, movably disposed within hollow delivery lumens 1455a and 1455b. Delivery lumen 1455a and delivery lumen 1455b each extend between distal portion 1415 and proximal portion 1410. Delivery lumen 1455a and delivery lumen 1455b can be made from any suitable material, such as polymers and copolymers of polyamides, polyolefins, polyurethanes, and the like. Access to the proximal end of delivery lumen 1455a or delivery lumen 1455b for insertion of needle 1450a or 1450b, respectively, is provided through hub 1460.

One or both of delivery lumen 1455a and delivery lumen 1455b may be used to deliver a free pro-healing treatment agent or a pro-healing agent encapsulated, suspended, disposed within or loaded into a biodegradable carrier, include to a treatment site. In some embodiments, catheter assembly 1400 includes one delivery lumen. In some applications, catheter assembly 1400 may be used to percutaneously deliver a free pro-healing agent or a pro-healing agent encapsulated, suspended, disposed within or loaded into a biodegradable carrier to a treatment site.

Figure 15:
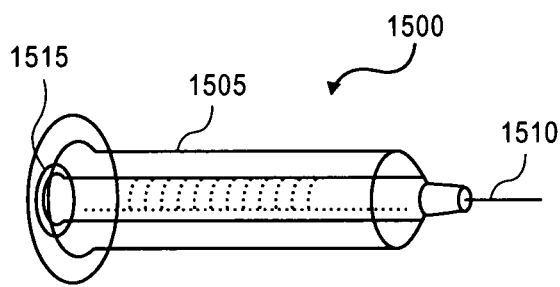
FIG. 15 shows a syringe to deliver a treatment agent introduced into the blood vessel.

FIG. 15 illustrates an embodiment of a syringe which may be used pursuant to the present invention. Syringe 1500 may include a body 1505, a needle 1510 and a plunger 1515. A shaft of plunger 1515 has an exterior diameter slightly less than an interior diameter of body 1505 so that plunger 1515 can, in one position, retain a substance in body 1505 and, in another position, push a substance through needle 1510. Syringes are known by those skilled in the art. In some applications, syringe 1500 may be applied directly to a treatment site during an open-chest surgery procedure to deliver a free pro-healing agent or a pro-healing agent encapsulated, suspended, disposed within or loaded into a biodegradable carrier to a treatment site.

The above delivery devices and systems are representative of devices that may be used to deliver a free pro-healing treatment agent or a pro-healing agent encapsulated, suspended, disposed within or loaded into a biodegradable carrier to an endothelium. For example, treatment agents suitable to form an in situ layer for wall modification described above with reference to FIG. 5 may be introduced at a treatment site with a variety of delivery devices. These devices include delivery through pores of a porous balloon, see. FIGS. 6-10 and the accompanying text, or through a saturated sponge mounted on a distal end of a delivery system, see, for example, FIG. 11. In addition, the vessel may be balloon occluded proximal and distal to the target site as shown in FIG. 2 and FIG. 3 (e.g., a dog-bone shape balloon). Additional treatment agents that might be added subsequently to an in situ formed layer may be deposited through the same deposition devices that are used to introduce the hydrogel coating or through a second device.

Methods of Treatment

Figure 16:
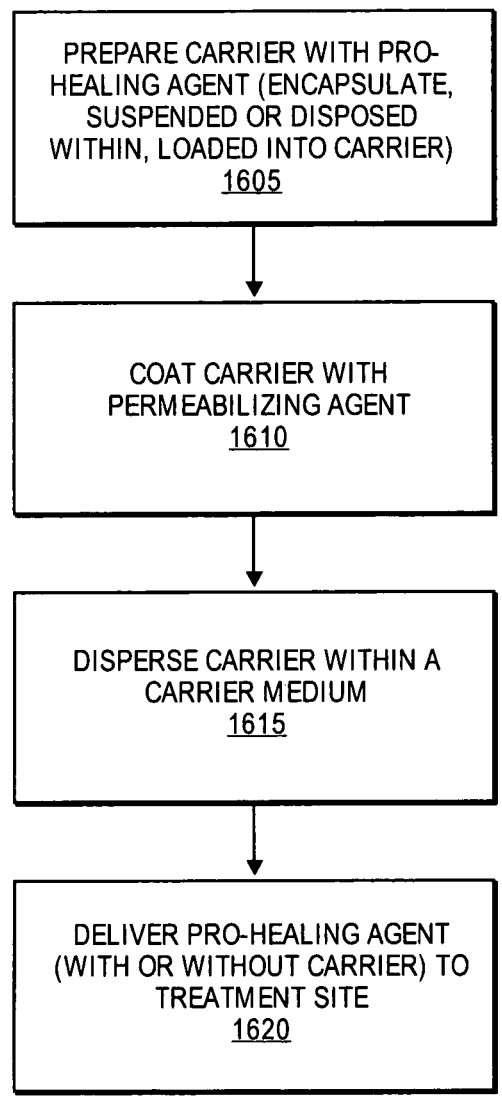
FIG. 16 schematically shows a method for preparing a pro-healing agent in preparation for delivery to a treatment site.

In some embodiments, at least one pro-healing agent encapsulated, suspended, disposed within or loaded into a biodegradable carrier can be delivered to a treatment site. FIG. 16 schematically illustrates a method of preparing a pro-healing agent for delivery to a treatment site. In some methods, a pro-healing agent can be encapsulated, suspended, disposed within or loaded into a biodegradable carrier by the methods described previously (1605). The carrier can then be coated with a permeabilizing agent such as those described previously (1610). Thereafter, the carrier can be suspended within a carrier medium in preparation for delivery. Examples of carrier media include, but are not limited to, phosphate buffered saline, serum and plasma (1615). The carrier medium can be in a concentration of between about 1 mM and 5000 mM. In some applications, about 10 μL to about 2000 μL of pro-healing agent (with or without the carrier) can be delivered to a treatment site (1620). In applications in which a sustained-release carrier is used, the release of the pro-healing agent can be from between about 2 hours to about 60 days.

In some embodiments, more than one pro-healing agent encapsulated, suspended, disposed within or loaded into a biodegradable carrier can be delivered to a treatment site. For example, in some embodiments, estradiol and cyclic RGD can be encapsulated, suspended, disposed within or loaded into a biodegradable carrier for delivery to a treatment site. In some embodiments, a first pro-healing agent can be encapsulated, suspended, disposed within or loaded into a first biodegradable carrier and a second pro-healing agent can be encapsulated, suspended, disposed within or loaded into a second biodegradable carrier for delivery to a treatment site. Any combination of pro-healing and carrier is contemplated by the present invention.

From the foregoing detailed description, it will be evident that there are a number of changes, adaptations and modifications of the present invention which come within the province of those skilled in the part. The scope of the invention includes any combination of the elements from the different species and embodiments disclosed herein, as well as subassemblies, assemblies and methods thereof. However, it is intended that all such variations not departing from the spirit of the invention be considered as within the scope thereof.

What is claimed is:

1. A method comprising:
introducing a catheter device to a denuded or damaged endothelium treatment area in a blood vessel of a human subject, wherein the catheter device comprises a porous balloon and a cover member for covering a porous surface of the balloon, the cover member having a window through which a portion of the porous surface is exposed to allow for targeted delivery of a fluid solution through the porous surface;
isolating the denuded or damaged endothelium treatment area in the blood vessel, wherein isolating comprises aligning the window with the denuded or damaged endothelium treatment area such that the porous surface is exposed to the treatment area; and
after isolating, delivering the fluid solution to the denuded or damaged endothelium treatment area through the porous surface, the fluid solution comprising a pro-healing agent disposed within a biodegradable carrier, wherein the pro-healing agent is an extra-cellular binding protein, and wherein the pro-healing agent has a property that accelerates re-endothelialization, and wherein the carrier is one of a liposome, a polymerosome, a micelle or a particle.

2. The method of claim 1, wherein the particle is one of a microsphere, a nanosphere, a microrod or a nanorod.

3. The method of claim 1, wherein the pro-healing agent has a characteristic selected from the group consisting of (a) providing docking sites for endothelium progenitor cells and (b) chemoattracting endothelium progenitor cells.

4. The method of claim 1 wherein the extra-cellular binding protein is selected from the group consisting of arginine-glycine-aspartic acid peptide sequence (RGD), cyclic RGD, serine-isoleucine-lysine-valine-alanine-valine, and tyrosine-isoleucine-glycine-serine-arginine.

5. The method of claim 1 wherein the extra-cellular binding protein is a growth factor.

6. The method of claim 5 wherein the growth factor is selected from the group consisting of isoforms of vasoendothelial growth factor, fibroblast growth factor, Del 1, hypoxia inducing factor, monocyte chemoattractant protein, nicotine, platelet derived growth factor, insulin-like growth factor 1, transforming growth factor, hepatocyte growth factor, estrogens, follistatin, proliferin, prostaglandin E1 and E2, tumor necrosis factor, interleukin 8, hematopoietic growth factors, erythropoietin, granulocyte-colony stimulating factors and platelet-derived endothelial growth factor.

7. The method of claim 1 wherein the extra-cellular binding protein is a hormone.

8. The method of claim 7 wherein the hormone is estradiol.

9. The method of claim 1 wherein the cover member is a sheath positioned outside of the balloon.

10. The method of claim 1 wherein the cover member is a liner positioned inside of the balloon.

11. The method of claim 1 wherein the extra-cellular binding protein is an anti-inflammatory.

12. A method comprising:
isolating a damaged vascular segment in a human subject using a catheter device, the catheter device having a first balloon and a second balloon positioned at opposite ends of an inflatable cannula, wherein isolating comprises (1) positioning the first balloon proximal to the damaged vascular segment, (2) positioning the second balloon distal to the damaged vascular segment, and (3) separately inflating the first balloon and the second balloon; and
indirectly increasing endothelial functionality of the damaged vascular segment by delivering a solution comprising a pro-healing agent disposed within a biodegradable carrier to the isolated vascular segment between the first balloon and the second balloon of the catheter device, wherein the pro-healing agent is a growth factor, and wherein the pro-healing agent has a property that accelerates re-endothelialization, and wherein the carrier is one of a liposome, a polymerosome, a micelle, or a particle.

13. The method of claim 12, wherein the particle is one of a microsphere, a nanosphere, a microrod or a nanorod.

14. The method of claim 12, wherein delivering further comprises inflating the inflatable cannula to drive the solution comprising the pro-healing agent into the isolated vascular segment.

15. The method of claim 12, wherein the pro-healing agent has a characteristic selected from the group consisting of (a) providing docking sites for endothelium progenitor cells and (b) chemoattracting endothelium progenitor cells.

16. A method of treatment comprising:
isolating a lumen of a blood vessel in a human subject; and
delivering a solution comprising a pro-healing agent disposed within a biodegradable carrier to a treatment site within the isolated lumen of the blood vessel, wherein delivering comprises targeting delivery of the solution to the treatment site by delivering the solution through only a portion of a catheter device positioned adjacent to the treatment, and
wherein the pro-healing agent is adapted to indirectly (a) accelerate re-endothelialization of a denuded vascular segment relative to non-treatment induced re-endothelialization or (b) rehabilitate endothelial functionality of a damaged vascular segment relative to non-treatment induced rehabilitation, wherein the pro-healing agent is an extra-cellular binding protein, and wherein the pro-healing agent has a property that accelerates re-endothelialization, and wherein the carrier is one of a liposome, a polymerosome, a micelle or a particle.

17. The method of claim 16, wherein the particle is one of a microsphere, a nanosphere, a microrod or a nanorod.

18. The method of claim 16, wherein the catheter device used to deliver the pro-healing agent is one of a porous balloon catheter, or a double balloon catheter.

19. The method of claim 16, wherein the pro-healing agent has a characteristic selected from the group consisting of (a) providing docking sites for endothelium progenitor cells and (b) chemoattracting endothelium progenitor cells.

20. The method of claim 16 wherein the catheter device comprises a porous balloon and a sheath positioned over the porous balloon, the sheath having a window to expose only a portion of the porous balloon adjacent to the treatment site such that delivery of the solution is targeted to the treatment site.

21. The method of claim 16 wherein the catheter device comprises a first balloon and a second balloon positioned at opposite ends of an inflatable cannula, wherein the first balloon, the second balloon and the inflatable cannula are inflatable using separate inflation cannulas.

* * * * *